US009884091B2

(12) United States Patent
Holscher

(10) Patent No.: US 9,884,091 B2
(45) Date of Patent: Feb. 6, 2018

(54) TREATMENT OF NEUROLOGICAL DISEASES

(71) Applicant: Lancaster University Business Enterprises Limited, Lancaster (GB)

(72) Inventor: Christian Holscher, Lancashire (GB)

(73) Assignee: Lancaster University Business Enterprises Limited, Lancaster (GB)

(*) Notice: Subject to any disclaimer, the term of this patent is extended or adjusted under 35 U.S.C. 154(b) by 0 days.

(21) Appl. No.: 14/799,143

(22) Filed: Jul. 14, 2015

(65) Prior Publication Data

US 2016/0015788 A1 Jan. 21, 2016

(30) Foreign Application Priority Data

Jul. 15, 2014 (GB) .................................. 1412578.5

(51) Int. Cl.
*A61K 38/26* (2006.01)
*A61K 38/22* (2006.01)

(52) U.S. Cl.
CPC .............................. *A61K 38/2278* (2013.01)

(58) Field of Classification Search
None
See application file for complete search history.

(56) References Cited

U.S. PATENT DOCUMENTS

2012/0322725 A1* 12/2012 Dimarchi ............... A61K 38/26
514/4.8

FOREIGN PATENT DOCUMENTS

| WO | WO 1998/008871 A1 | 3/1998 |
|---|---|---|
| WO | WO 2011/163012 A2 | 12/2011 |
| WO | WO 2013/074910 A1 | 5/2013 |
| WO | WO 2014/152460 A2 | 9/2014 |

OTHER PUBLICATIONS http://www.mayoclinic.org/diseases-conditions/diabetic-neuropathy/basics/definition/con-20033336, Accessed Apr. 12, 2016.*
The National Institute of Neurological Disorders and Stroke (NINDS) (http://www.ninds.nih.gov/disorders/disorder_index.htm, accessed Apr. 11, 2016).*
Autism spectrum disorder, NINDS (http://www.ninds.nih.gov/disorders/autism/autism.htm, accessed Apr. 11, 2016).*
Spinal cord tumors, NINDS (http://www.ninds.nih.gov/disorders/brainandspinaltumors/brainandspinaltumors.htm.*
Irwin et al. (A Novel, Long-Acting Agonist of Glucose-Dependent Insulinotropic Polypeptide Suitable for Once Daily Administration in Type 2 Diabetes', The Journal of Pharmacology and Experimental Therapeutics, 314;1187-1194, 2005).*
Caslo (Peptide Modification, Aug. 24, 2013).*
Picconi et al. (Synaptic dysfunction in Parkinson's Disease; Adv. Exp Med Biol. 2012;970:553-72).*
Duffy, A.M. et al.: "Novel GIP Incretin Analogues as a Potential Treatment for Alzheimer Disease," Society for Neuroscience, Annual Conference, San Diego, Nov. 9, 2013, Presentation Abstract 41.23.
Campbell, Jonathan E. et al.: "Pharmacology, Physiology, and Mechanisms of Incretin Hormone Action." Cell Metabolism, vol. 17, Jun. 4, 2013, pp. 1-19.
Duffy, A.M. et al.: "The Incretin Analogue D-ALA$^2$GIP Reduces Plaque Load, Astrogliosis and Oxidative Stress in an App/PS1 Mouse Model of Alzheimer's Disease," Neuroscience, vol. 228 (2013), pp. 294-300.
Faivre, Emilie et al.: "D-Ala$^2$GIP Facilitated Synaptic Plasticity and Reduces Plaque Load in Aged Wild Type Mice and in an Alzheimer's Disease Mouse Model," Journal of Alzheimer's Disease, vol. 35 (2013), pp. 267-283.
Lovshin, Julie A. et al.: "Incretin-based Therapies for Type 2 Diabetes Mellitus," Nature Review/Endocrinology, vol. 5, May 2009, pp. 262-269.
McClean, Paula L. et al.: "Glucagon-like Peptide-1 Analogues Enhance Synaptic Plasticity in the Brain: A Link Between Diabetes and Alzheimer's Disease," European Journal of Pharmacology, vol. 630, 2010, pp. 158-162.
Gault, Victor A. et al.: "GLP-1 Agonists Facilitate Hippocampal LTP and Reverse the Impairment of LTP Induced by Beta-amyloid," European Journal of Pharmacology, vol. 587, 2008, pp. 112-117.
Radde, Rebecca et al.: "Aβ42-driven Cerebral Amyloidosis in Transgenic Mice Reveals Early and Robust Pathology," EMBO Reports, vol. 7, No. 9, 2006, pp. 940-946.
Bertilsson, Göran et al.: "Peptide Hormone Exendin-4 Stimulates Subventricular Zone Neurogenesis in the Adult Rodent Brain and Induces Recovery in an Animal Model of Parkinson's Disease," Journal of Neuroscience Research, vol. 86, 2008, pp. 326-338.
Finan, Brian et al.: "Unimolecular Dual Incretins Maximize Metabolic Benefits in Rodent, Monkeys, and Humans." Science Translational Medicine, vol. 5, Issue 209, Oct. 30, 2013, pp. 1-8, Supplementary Material.
Finan, Brian et al.: "Unimolecular Dual Incretins Maximize Metabolic Benefits in Rodent, Monkeys, and Humans." Science Translational Medicine, vol. 5, Issue 209, Oct. 30, 2013, pp. 18.
Aviles-Olmos, Iciar, et al.: "Motor and Cognitive Advantages Persist 12 Months After Exenatide Exposure in Parkinson's Disease," Journal of Parkinson's Disease, vol. 4, No. 3, 2014, pp. 337-344.
Hölscher, Christian et al.: "Neuroprotective Effects of D-Ala$^2$GIP on Alzheimer's Disease Biomarkers in an APP/PS1 Mouse Model," Alzheimer's Research & Therapy, 2013, pp. 1-24.
Gault, Victor A. et al.: "Protease-Resistant Glucose-Dependent Insulinotropic Polypeptide Agonists Facilitate Hippocampal LTP and Reverse the Impairment of LTP Induced by Beta-Amyloid," J Neurophysiology, vol. 99, Issue 4, (Apr. 2008), pp. 1590-1595.

(Continued)

*Primary Examiner* — James H Alstrum-Acevedo
*Assistant Examiner* — Tara L Martinez
(74) *Attorney, Agent, or Firm* — Knobbe, Martens, Olson & Bear, LLP

(57) ABSTRACT

Methods treat neurological disorders, for example neurodegenerative disorders such as Alzheimer's disease, Parkinson's disease and stroke. Particularly although not exclusively, GIP/GLP-1 co-agonist peptide is used in the treatment of such neurological disorders. Pharmaceutical compositions include a GIP/GLP-1 co-agonist peptide for use in treatment of such disorders.

13 Claims, 8 Drawing Sheets

(56) References Cited

OTHER PUBLICATIONS

Nyberg, Jenny et al.: "Immunohistochemical Distribution of Glucose-Dependent Insulintropic Polypeptide in the Adult Rat Brain," Journal of Neuroscience Research, vol. 85, 2007, pp. 2099-2119.

Faivre, Emilie et al.: "Glucose-dependent Insulinotropic Polypeptide Receptor Knockout Mice are Impaired in Learning, Synaptic Plasticity, and Neurogenesis," J Neurophysiology, vol. 105, 2011, pp. 1574-1580.

Ohara, T. et al.: "Glucose Tolerance Status and Risk of Dementia in the Community: The Hiyasama Study," Neurology, vol. 77, Sep. 20, 2011, pp. 1126-1134.

Aviles-Olmos, Iciar et al.: "Exenatide and the Treatment of Patients with Parkinson's Disease," The Journal of Clinical Investigation, vol. 123, No. 6, Jun. 3, 2013, pp. 2730-2736.

Bomfim, Theresa R. et al.: "An Anti-Diabetes Agent Protects the Mouse Brain from Defective Insulin Signaling Caused by Alzheimer's Disease-associated AβOligomers," The Journal of Clinical Investigation, vol. 122, No. 4, Apr. 2012, pp. 1339-1353.

Li, Yazhou et al.: "GLP-1 Receptor Stimulation Preserves Primary Cortical and Dopaminergic Neurons in Cellular and Rodent Models of Stroke and Parkinsonism," PNAS, vol. 106, No. 4, Jan. 27, 2009, pp. 1285-1290.

McClean, Paula L. et al.: "The Diabetes Drug Liraglutide Prevents Degenerative Processes in a Mouse Model of Alzheimer's Disease," The Journal of Neuroscience, vol. 31, No. 17, Apr. 27, 2011, pp. 6587-6594.

McClean, Paula L. et al.: "Liraglutide can Reverse Memory Impairment, Synaptic Loss and Reduce Plaque Load in Aged APP/PS1 Mice, a Model of Alzheimer's Disease," Neuropharmacology, vol. 76, Part A, (2014), pp. 57-67.

Moloney, Aileen M. et al.: "Defects in IGF-1 Receptor, Insulin Receptor and IRS-1/2 in Alzheimer's Disease Indicate Possible Resistance to IGF-1 and Insulin Signaling," Neurobiology of Aging, vol. 31, Issue 2, (2010), pp. 224-243.

Harkavyi, Alexander et al.: "Glucagon-like Peptide 1 Receptor Stimulation Reverses Key Deficits in Distinct Rodent Models of Parkinson's Disease," Journal of Neuroinflamation, vol. 5, No. 19, May 21, 2008, pp. 1-9.

Hölscher, Christian, "Insulin, Incretins and Other Growth Factors as Potential Novel Treatments for Alzheimer's and Parkinson's Diseases," Biochemical Society Transactions, vol. 42, Issue 2 (2014), pp. 593-599.

Talbot, Konrad et al.: "Demonstrated Brain Insulin Resistance in Alzheimer's Disease Patients is Associated with IGF-1 Resistance, IRS-1 Dysregulation, and Cognitive Decline," The Journal of Clinical Investigation, vol. 122, No. 4, Apr. 2012, pp. 1316-1338.

Gengler, Simon et al.: "Val(8)GLP-1 Rescues Synaptic Plasticity and Reduces Dense Core Plaques in APP/PS1 Mice," Neurobiology of Aging, vol. 33, No. 2, Apr. 2010 (online), pp. 265-276.

GB Patent Search Report, dated Apr. 9, 2015, in Application No. GB1412578.5, filed Jul. 15, 2014.

Liu, W. et al.: "Neuroprotective effects of lixisenatide and liraglutide in the 1-methyl-4-phenyl-1, 2, 3, 6-tetrahydropyridine mouse model of PD," Neuroscience, vol. 303, 2015, pp. 42-50.

Day, J. W. et al.: "A new glucagon and GLP-1 co-agonist eliminates obesity in rodents," Nature Chemical Biology, vol. 5, 10, 2009, pp. 749-757.

* cited by examiner

Figure 8

SEQ ID No. 1:

YXEGTFTSDYSIYLDKQAAXEFVNWLLAGGPSSGAPPPS[Lys-C16]-NH2

X = amino-isobutyric acid

SEQ. ID No. 2

YXEGTFTSDYSIYLDKQAAXEFV[Cys-40kDaPEG]WLLAGGPSSGAPPPS[Lys-γE-C16]-NH2

X = amino-isobutyric acid

SEQ ID No. 3

Gly-Pro-Ser-Ser-Gly-Ala-Pro-Pro-Pro-Ser;

SEQ ID No. 4

Gly-Pro-Ser-Ser-Gly-Ala-Pro-Pro-Pro-Ser-Lys

SEQ ID No. 5

Gly-Pro-Ser-Ser-Gly-Ala-Pro-Pro-Pro-Ser-Cys

SEQ ID No. 6

Pro-Ser-Ser-Gly-Ala-Pro-Pro-Pro-Ser

SEQ. ID No. 7

Pro-Ser-Ser-Gly-Ala-Pro-Pro-Ser

SEQ ID No 8

HAEGTFTSDVSSYLEGQAAK EFIAWLVKGR G-OH

SEQ ID No.9

YAEGTFISDYSIAMDKIHQQDFVNWLLAQKGKKNDWKHNITQ-OH

SEQ ID No. 10

HAEGTFTSDVSSYLEGQAA[Lys- γE- C16 acyl]EFIAWLVRGRG-OH

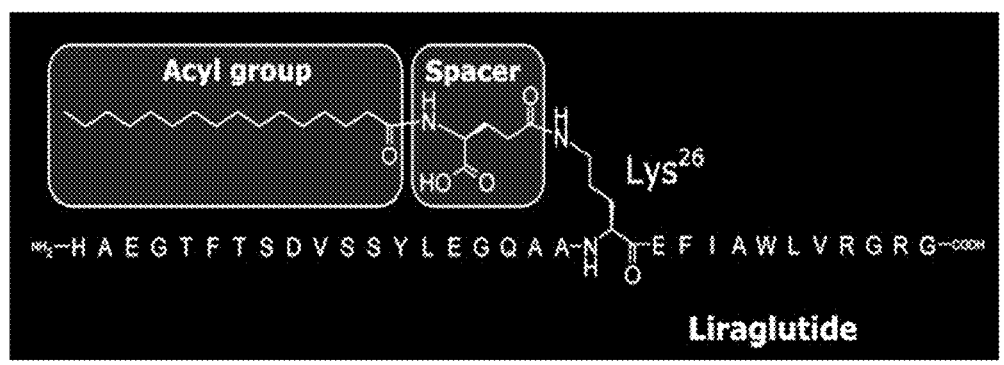

Figure 8 (Continued)

SEQ ID. No 11

Y*d*-AEGTFISDYSIAMDKIHQQDFVNWLLAQKGKK(γ-E-C16)NDWKHNITQ

SEQ ID No. 12

Tyr-Aib-Glu-Gly-Thr-Phe-Thr-Ser-Asp-Tyr-Ser-Ile-Tyr-Leu-Asp-Lys-Gln-Ala-Ala-Aib-Glu-Phe-Val-Xaa$^{24}$-Trp-Leu-Leu-Ala-Gly-Y1-R$^2$   (Formula I)

SEQUENCE LISTING

```
<160> NUMBER OF SEQ ID NOS: 12

<210> SEQ ID NO 1
<211> LENGTH: 40
<212> TYPE: PRT
<213> ORGANISM: Artificial Sequence
<220> FEATURE:
<223> OTHER INFORMATION: GIP/GLP1 co-agonist peptide
<220> FEATURE:
<221> NAME/KEY: VARIANT
<222> LOCATION: 2, 20
<223> OTHER INFORMATION: Xaa = amino-isobutyric acid
<220> FEATURE:
<221> NAME/KEY: VARIANT
<222> LOCATION: 40
<223> OTHER INFORMATION: Xaa = a saturated fatty acid moiety or
      palmitate covalently bonded to a Lys amino acid residue

<400> SEQUENCE: 1

Tyr Xaa Glu Gly Thr Phe Thr Ser Asp Tyr Ser Ile Tyr Leu Asp Lys
1               5                   10                  15

Gln Ala Ala Xaa Glu Phe Val Asn Trp Leu Leu Ala Gly Gly Pro Ser
            20                  25                  30

Ser Gly Ala Pro Pro Pro Ser Xaa
        35                  40

<210> SEQ ID NO 2
<211> LENGTH: 40
<212> TYPE: PRT
```

```
<213> ORGANISM: Artificial Sequence
<220> FEATURE:
<223> OTHER INFORMATION: GIP/GLP1 co-agonist peptide
<220> FEATURE:
<221> NAME/KEY: VARIANT
<222> LOCATION: 2, 20
<223> OTHER INFORMATION: Xaa = amino-isobutyric acid
<220> FEATURE:
<221> NAME/KEY: VARIANT
<222> LOCATION: 24
<223> OTHER INFORMATION: Xaa = Cys with a covalently linked PEG molecule
      having an average molecular weight of 40kDa
<220> FEATURE:
<221> NAME/KEY: VARIANT
<222> LOCATION: 40
<223> OTHER INFORMATION: Xaa = lysine residue connected to gamma-
      glutamate and C16, wherein C16 is a saturated fatty acid or
      palmitate

<400> SEQUENCE: 2

Tyr Xaa Glu Gly Thr Phe Thr Ser Asp Tyr Ser Ile Tyr Leu Asp Lys
 1               5                  10                  15

Gln Ala Ala Xaa Glu Phe Val Xaa Trp Leu Leu Ala Gly Gly Pro Ser
            20                  25                  30

Ser Gly Ala Pro Pro Pro Ser Xaa
        35                  40

<210> SEQ ID NO 3
<211> LENGTH: 10
<212> TYPE: PRT
<213> ORGANISM: Artificial Sequence
<220> FEATURE:
<223> OTHER INFORMATION: GIP/GLP1 co-agonist peptide

<400> SEQUENCE: 3

Gly Pro Ser Ser Gly Ala Pro Pro Pro Ser
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: GIP/GLP1 co-agonist peptide

<400> SEQUENCE: 4

Gly Pro Ser Ser Gly Ala Pro Pro Pro Ser Lys
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: GIP/GLP1 co-agonist peptide

<400> SEQUENCE: 5

Gly Pro Ser Ser Gly Ala Pro Pro Pro Ser Cys
 1               5                  10

<210> SEQ ID NO 6
<211> LENGTH: 9
<212> TYPE: PRT
<213> ORGANISM: Artificial Sequence
<220> FEATURE:
<223> OTHER INFORMATION: GIP/GLP1 co-agonist peptide

<400> SEQUENCE: 6
```

-continued

Pro Ser Ser Gly Ala Pro Pro Pro Ser
1               5

<210> SEQ ID NO 7
<211> LENGTH: 8
<212> TYPE: PRT
<213> ORGANISM: Artificial Sequence
<220> FEATURE:
<223> OTHER INFORMATION: GIP/GLP1 co-agonist peptide

<400> SEQUENCE: 7

Pro Ser Ser Gly Ala Pro Pro Ser
1               5

<210> SEQ ID NO 8
<211> LENGTH: 31
<212> TYPE: PRT
<213> ORGANISM: Artificial Sequence
<220> FEATURE:
<223> OTHER INFORMATION: Human Glucagon-like Peptide-1

<400> SEQUENCE: 8

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 9
<211> LENGTH: 42
<212> TYPE: PRT
<213> ORGANISM: Artificial Sequence
<220> FEATURE:
<223> OTHER INFORMATION: Human Gastric inhibitory peptide
      (glucose-dependent insulinotropic peptide)

<400> SEQUENCE: 9

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 10
<211> LENGTH: 31
<212> TYPE: PRT
<213> ORGANISM: Artificial Sequence
<220> FEATURE:
<223> OTHER INFORMATION: Liraglutide
<220> FEATURE:
<221> NAME/KEY: VARIANT
<222> LOCATION: 20
<223> OTHER INFORMATION: Xaa = Lysine residue comprising gamma-glutamate
      linker between C16 palmitoyl group and lysine side-chain amino
      group

<400> SEQUENCE: 10

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly
            20                  25                  30

<210> SEQ ID NO 11
<211> LENGTH: 43
<212> TYPE: PRT
<213> ORGANISM: Artificial Sequence

```
<220> FEATURE:
<223> OTHER INFORMATION: synthetic peptide
<220> FEATURE:
<221> NAME/KEY: VARIANT
<222> LOCATION: 2
<223> OTHER INFORMATION: Xaa = D-Alanine
<220> FEATURE:
<221> NAME/KEY: VARIANT
<222> LOCATION: 34
<223> OTHER INFORMATION: Xaa = gamma-glutamate linked to C16, wherein
      C16 is a saturated fatty acid or a palmitoyl group

<400> SEQUENCE: 11

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
                20                  25                  30

Lys Xaa Asn Asp Trp Lys His Asn Ile Thr Gln
        35                  40

<210> SEQ ID NO 12
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 2, 20
<223> OTHER INFORMATION: Xaa = alpha amino isobutyric acid
<220> FEATURE:
<221> NAME/KEY: VARIANT
<222> LOCATION: 24
<223> OTHER INFORMATION: Xaa = Asn or Cys
<220> FEATURE:
<221> NAME/KEY: VARIANT
<222> LOCATION: 30
<223> OTHER INFORMATION: Xaa = absent or at least eight amino acid
      molecules

<400> SEQUENCE: 12

Tyr Xaa Glu Gly Thr Phe Thr Ser Asp Tyr Ser Ile Tyr Leu Asp Lys
1               5                   10                  15

Gln Ala Ala Xaa Glu Phe Val Xaa Trp Leu Leu Ala Gly Xaa
                20                  25                  30
```

TREATMENT OF NEUROLOGICAL DISEASES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims priority to and the benefit of UK Patent Application No. 1412578.5 filed in the UK Intellectual Property Office on Jul. 15, 2014, the entire contents of which are incorporated herein by reference.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 21122546.TXT, the date of creation of the ASCII text file is Jul. 14, 2015, and the size of the ASCII text file is 5.43 KB.

BACKGROUND

Field of the Invention

Aspects and embodiments of the present invention relate to the treatment of neurological disorders, for example neurodegenerative disorders such as Alzheimer's disease, Parkinson's disease and stroke. Particularly although not exclusively, the present invention relates at least in part to a GIP/GLP1 co-agonist peptide for use in the treatment of such neurological disorders. Also included in the present invention are inter alia pharmaceutical compositions comprising a GIP/GLP1 co-agonist peptide for use in treatment of such disorders, together with methods of treating such disorders as well as other subject matter.

Description of the Related Art

Alzheimer's disease is a chronic neurodegenerative disorder for which there is no cure. Currently prescribed medication only temporarily relieves some of the symptoms. The main hallmarks of the disease are disorientation, loss of memory, loss of neurons and synapses in the brain, the accumulation of beta-amyloid protein in the brain (amyloid plaques), and intracellular aggregation of hyperphosphorylated tau protein (tangles) (LaFerla and Oddo, 2005; Blennow et al., 2006).

Parkinson' disease is also a chronic neurodegenerative disease for which only delaying medication is available. The main hallmarks are tremor, rigor, and a loss of ability to move, the degeneration of neurons in the basal brain (substantia nigra) and the loss of release of the neurotransmitter, dopamine (Shen, 2010).

Type 2 diabetes (T2DM) has been identified as a risk factor for AD and PD (Hölscher, 2014), indicating that insulin signalling impairment may be a factor in initiating or accelerating the development of AD. Epidemiological studies found a clear correlation between T2DM and the risk of developing AD or other neurodegenerative disorders at a later stage (Luchsinger et al., 2004; Ristow, 2004; Ohara et al., 2011). It was also shown that insulin signalling in the brain is desensitised in AD patients. Recent studies demonstrated that brains of AD patients had increased levels of inactivated phosphorylated insulin receptors and IRS-1 second messengers, which are both indicative of insulin desensitisation (Moloney et al., 2010; Bomfim et al., 2012; Talbot et al., 2012). In PD, insulin signalling was also found to be impaired and linked to disease progression (Morris et al., 2011; Cereda et al., 2012).

Glucagon-like peptide (GLP-1) is an endogenous 31-amino acid peptide incretin hormone (Baggio and Drucker, 2007). GLP-1 receptor stimulation enhances beta-cell proliferation in the pancreas by activating stem cell proliferation, facilitates glucose-dependent insulin secretion and lowers blood glucose in patients with T2DM (Lovshin and Drucker, 2009). Three GLP-1 analogues are currently on the market as a treatment for diabetes, exendin-4 (Byetta®), lixisenatide (Lyxumia®) and liraglutide (SEQ ID No. 10) (Victoza®) (Campbell and Drucker, 2013; Elkinson and Keating, 2013).

Glucose-dependent insulinotropic peptide (GIP), also known as gastric inhibitory polypeptide, is a 42-amino acid incretin hormone which activates pancreatic islets to enhance insulin secretion and to help reduce postprandial hyperglycaemia, similar to GLP-1 (Gault et al., 2003). GIP is a member of the seretin/glucagon family of neuroregulatory polypeptides which also include the growth hormone releasing factor. It is expressed in pancreatic alpha cells, endocrine cells, and also in neurons in the brain (Nyberg et al., 2007; Campbell and Drucker, 2013). GIP has also been shown to promote pancreatic beta-cell growth, differentiation, proliferation and cell survival, documenting its growth-hormone properties (Gault et al., 2003). Therefore, research is on-going to develop GIP as a therapeutic tool for T2DM treatment (Irwin et al., 2006). There are currently no GIP analogues authorised for the treatment of T2D.

Dual agonist peptides which target more than one receptor are being considered for the treatment of T2D. Several GIP/GLP-1 co-agonist peptides are currently in development for the treatment of T2D. However, there are currently no GIP/GLP-1 dual agonists authorised for use to treat T2D.

Recent investigations of the neuroproperties of GLP-1 and GIP have indicated that these peptides may play a role in preventing neurodegenerative hallmarks in several mouse models of Alzheimer's disease (AD) and also in animal models of Parkinson's disease (PD).

Insulin as well as the incretins not only have growth-factor like properties in the brain, but also modulate synaptic activity (Hölscher, 2014). Synapses are the contacts between neurons, and they are important for memory formation and information processing in the brain. Direct injection of GLP-1 or long-lasting GLP-1 analogues into the brain markedly enhanced long-term potentiation of synaptic transmission (LTP) in the hippocampus, a brain area that is involved in memory formation. LTP is considered a cellular correlate of memory formation (Bliss and Collingridge, 1993). The GLP-1 analogue, liraglutide, has been shown to upregulate LTP in the rat brain (McClean et al., 2010).

In addition, GLP-1 analogues were able to prevent the impairment of LTP that was induced by beta-amyloid fragments (Gault and Hölscher, 2008a; McClean et al., 2011; Gengler et al., 2012; Han et al., 2013). This impairment of LTP by amyloid protein may be the mechanism by which amyloid causes memory loss (Cleary et al., 2005). A study testing liraglutide (SEQ ID No. 10) in an APP/PS1 mouse model of AD showed that the drug can prevent the impairment in memory formation and synaptic plasticity, the reduction of total numbers of synapses, normalise stem cell proliferation and neurogenesis in the dentate gyrus, reduce the inflammation response, and furthermore reduce amyloid plaque load in the cortex and total amyloid levels in the brain (McClean et al., 2011). In another study, liraglutide (SEQ ID No. 10) also had protective and regenerative effects in very old transgenic mice, demonstrating that even at an advanced stage of disease progression, memory can be improved and plaque load be reduced to some degree (McClean and Hölscher, 2013).

Based on these findings in animal models, a clinical trial of liraglutide (SEQ ID No. 10) in AD patients has started.

Furthermore, one prior art study has investigated the effects of exendin-4 in the 6-hydroxydopamine model of PD. After the lesion was induced, rats were treated with exendin-4 and a protection of motor activity was observed. Histological analysis showed that exendin-4 significantly increased the number of both tyrosine hydroxylase- and vesicular monoamine transporter 2-positive neurons in the substantia nigra (Bertilsson et al., 2008). In a second study, two rodent models of PD, 6-hydroxydopamine (6-OHDA) and lipopolysaccaride (LPS), were used to test the effects of exendin-4. Motor control was much improved in the drug group, and striatal tissue concentrations of dopamine were markedly higher. In addition, exendin-4 reversed the loss of extracellular DA in the striatum (Harkavyi et al., 2008).

Based on these studies, a clinical trial of exendin-4 in PD patients has been initiated. This study reported that in several motor assessments and in a cognitive test patients had improved, and the improvements were maintained even after the drug had been discontinued for 12 months (Aviles-Olmos et al., 2013; Aviles-Olmos et al., 2014).

Studies have also been carried out to determine whether GIP or GIP analogues have an effect in AD. It has been found that GIP analogues can prevent the LTP impairment that beta-amyloid fragments induce on synaptic transmission in the brain (Gault and Hölscher, 2008b). In a GIP receptor-deletion mouse strain, LTP was also impaired, and paired-pulse facilitation was reduced, indicating that the release of synaptic vesicles is reduced (Faivre et al., 2011). The long-lasting GIP analogue D-Ala$^2$-GIP also had neuroprotective effects in an APP/PS1 mouse model of AD. In 12 months old mice, synaptic plasticity in area CA1 of the hippocampus and spatial memory formation was impaired in APP/PS1 mice but was unimpaired in D-Ala$^2$-GIP treated APP/PS1 mice. In addition, the amyloid plaque load was much reduced, showing impressive effects in reducing the main hallmarks of AD (Faivre and Hölscher, 2013b).

In aged 19 month old AD mice, the drug was still able to reverse some of the AD symptoms such as synapse loss (Faivre and Hölscher, 2013a). In a longitudinal study, oxidative stress and the inflammation response in the brain was much reduced in APP/PS1 mice (Duffy and Hölscher, 2013b). This suggests that these analogues have neuroprotective properties in AD and protect synapses from the detrimental effects of beta-amyloid.

There remains a need to identify treatments for neurological disorders such as for example the neurodegenerative diseases, Alzheimer's disease and Parkinson's disease.

SUMMARY

It is an aim of certain embodiments of the present invention to at least partly mitigate the problems associated with the prior art.

It is an aim of certain embodiments of the present invention to provide a therapeutic peptide for use in the treatment and/or lessening the likelihood of occurrence, or even prevention of a neurodegenerative disorder such as for example Alzheimer's disease and/or Parkinson's disease.

It is an aim of certain embodiments of the present invention to provide a GIP/GLP-1 dual agonist peptide which has a superior property as compared to a GLP-1 mono agonist, for use in the treatment and/or lessening the likelihood of occurrence, or even prevention of a neurological disorder. Examples of superior properties include for example a greater decrease in beta-amyloid plaque load and/or reduction of motor skill impairment.

It is an aim of certain embodiments of the present invention to provide a GIP/GLP-1 dual agonist peptide which has a superior property as compared to a GIP mono agonist. Examples of superior properties include for example a greater decrease in beta-amyloid plaque load and/or reduction of motor skill impairment.

It is an aim of certain embodiments of the present invention to provide a GIP/GLP-1 dual agonist peptide for use in the treatment and/or lessening the likelihood of occurrence, or even prevention of a neurodegenerative disorder such as for example Alzheimer's disease and/or Parkinson's disease.

In a first aspect of the present invention, there is provided a GIP/GLP-1 co-agonist peptide, or a derivative or a pharmaceutically acceptable or solvate of the peptide or the derivative, for use in the treatment and/or prophylaxis of a neurological disorder. Aptly, the co-agonist peptide has a GLP-1 percentage potency within about 10-fold of the GIP percentage potency.

In one aspect of the present invention, there is provided a GIP/GLP-1 co-agonist peptide or a pharmaceutically acceptable salt or solvate thereof for use in the treatment and/or prophylaxis of a neurological disorder, wherein the co-agonist peptide is represented by the general Formula I:

[SEQ ID No. 12]
Tyr-Aib-Glu-Gly-Thr-Phe-Thr-Ser-Asp-Tyr-Ser-Ile-

Tyr-Leu-Asp-Lys-Gln-Ala-Ala-Aib-Glu-Phe-Val-

Xaa$^{24}$-Trp-Leu-Leu-Ala-Gly-Gly-Y1-R$^2$ (I)

wherein

Xaa$^{24}$ is selected from Asn and Cys;

Y1 is selected from absent or an extension comprising at least eight amino acid molecules; and R$^2$ is selected from —NH2 and —OH.

Aptly, the peptide is for use in the treatment and/or lessening the likelihood of occurrence, or even prevention of a neurodegenerative disorder, e.g. Alzheimer's disease or Parkinson's disease.

Also provided herein is a pharmaceutical composition which comprises a GIP/GLP-1 co-agonist peptide as described herein and a pharmaceutically acceptable carrier for use in the treatment and/or prophylaxis of a neurological disorder as described herein. Further provided in the present disclosure is a kit including such a pharmaceutical composition.

Also provided is a method of treating and/or lessening the likelihood of occurrence, or even preventing a neurological disorder as described herein, the method comprising administering a pharmaceutically effective amount of a GIP/GLP-1 co-agonist peptide as described herein to a subject in need thereof.

Further details of embodiments of the invention are provided below.

BRIEF DESCRIPTION OF THE DRAWINGS

Certain embodiments of the present invention are described in more detail below with reference to the following drawings:

As used herein, the abbreviation "DA1" refers to a GIP/GLP-1 co-agonist consisting of the amino acid sequence shown in SEQ ID No. 1.

As used herein, the abbreviation "DA2" refers to a GIP/GLP-1 co-agonist consisting of the amino acid sequence shown in SEQ ID No. 2.

Figure 1:
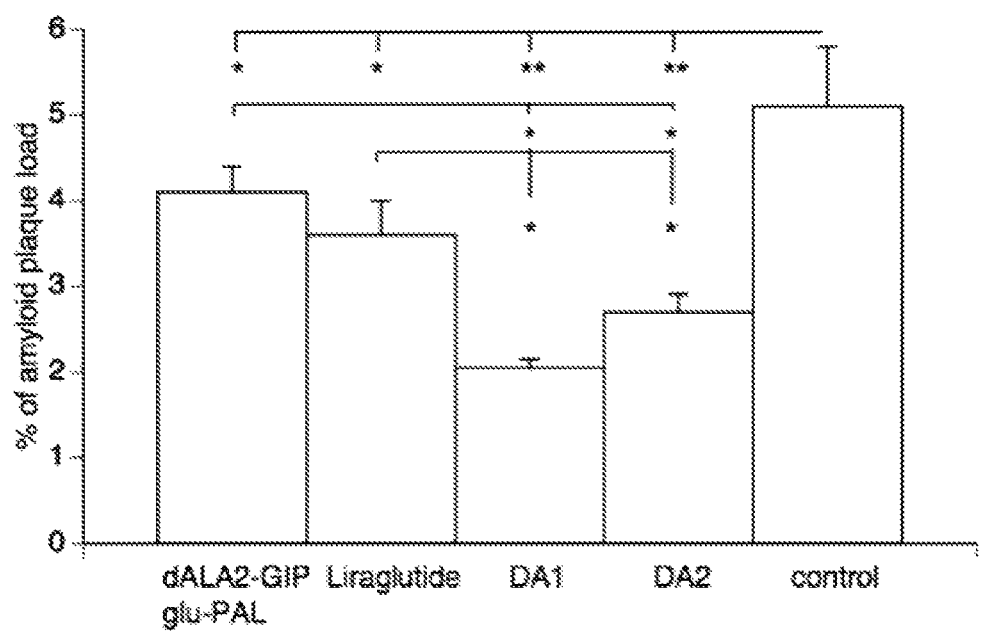

FIG. 1 illustrates an immunohistochemical measurement of beta-amyloid plaque load in the cortex of transgenic mice (Alzheimer's disease model). All peptides reduced the plaque load. Both co-agonist peptides (DA1 (SEQ ID NO. 1) and DA2 (SEQ ID NO. 2)) of embodiments of the present invention were superior to the single GIP or GLP-1 analogues and administration of DA1 (SEQ ID NO. 1) and DA2 (SEQ ID NO. 2) reduces beta-amyloid plaque load as quantified by beta amyloid immunohistochemistry and determination of the % area positive for beta amyloid in cross sections of the brain cortex. *=p<0.05, =p<0.01; *=p<0.005. N=5 per group.

Figure 2:
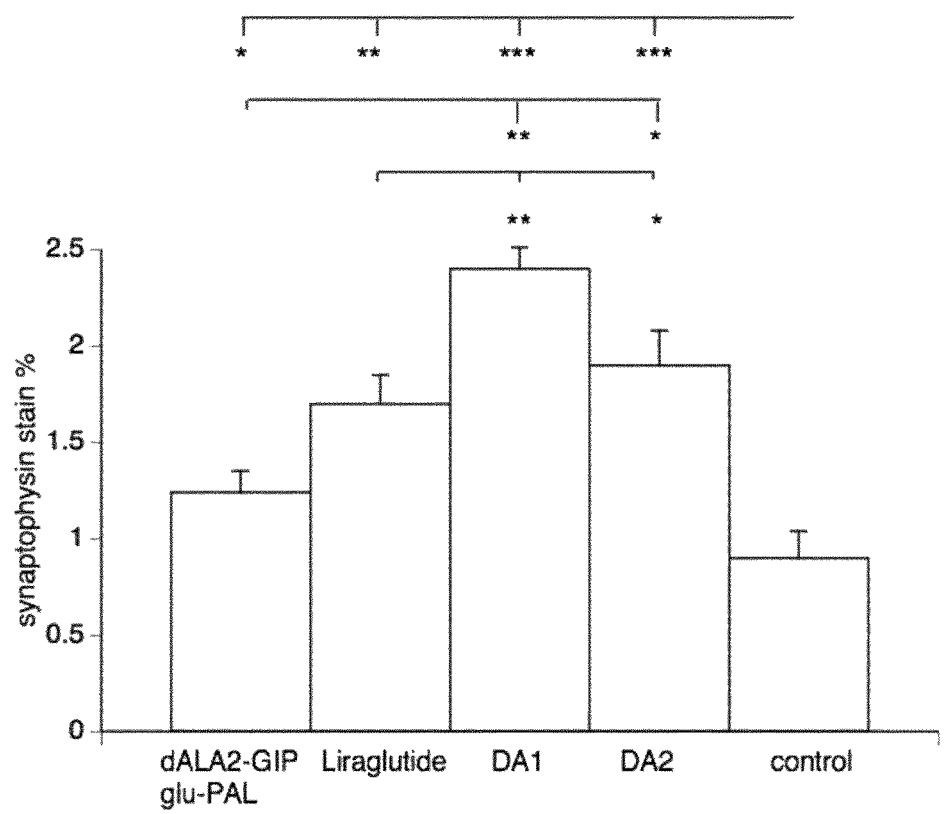

FIG. 2 is a graph illustrating that the DA1 (SEQ ID NO. 1) and DA2 (SEQ ID NO. 2) peptides protected from synapse loss in the cortex of transgenic mice (Alzheimer's disease model) as quantified by immunohistochemical measurement of synaptic densities in the cortex of the transgenic mice. All peptides protected from synapse loss. Both co-agonist peptides of embodiments of the present invention were superior to the single GIP or GLP-1 analogues. *=p<0.05, =p<0.01; *=p<0.005. N=5 per group.

Figure 3:
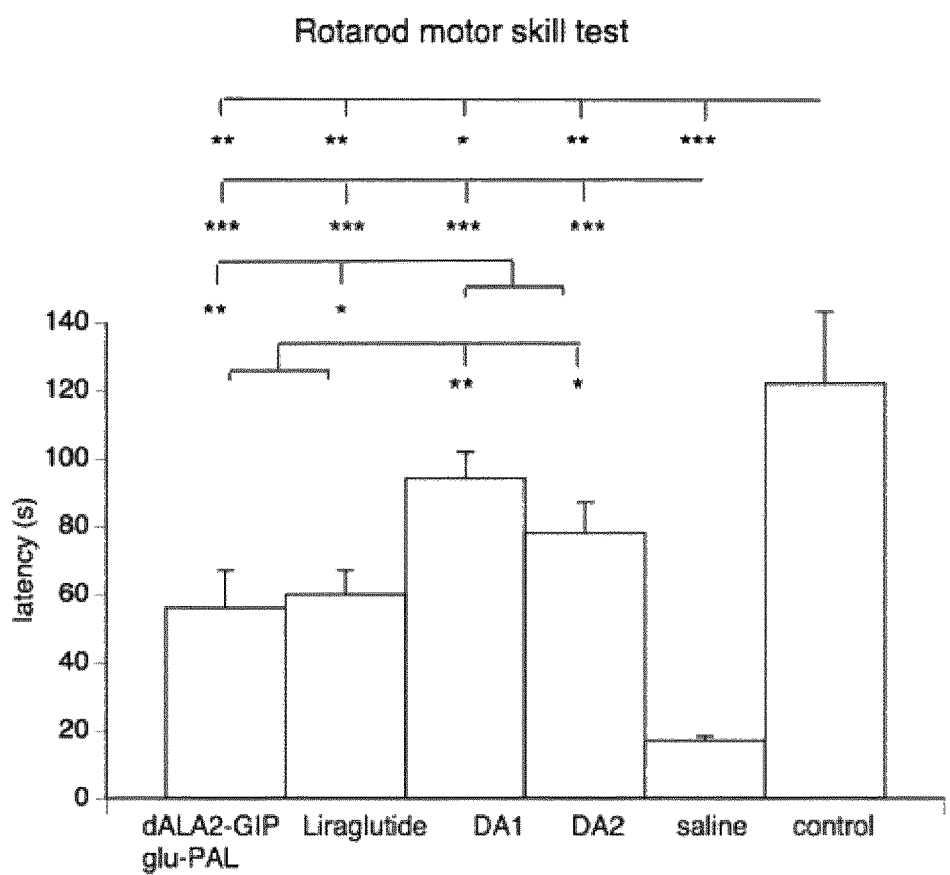

FIG. 3 is a graph illustrating that the DA1 (SEQ ID NO. 1) and DA2 (SEQ ID NO. 2) peptides protect mice from an impairment of motor skills induced by MPTP to reduce the levels of dopamine. A rotarod motor skill test was carried out as described below. Each animal's endurance time was recorded, and the average was calculated. Data were analysed using a one-way ANOVA with post-hoc Bonferroni tests. Both co-agonist peptides of embodiments of the present invention were superior to the single GIP or GLP-1 analogues. Control=wild type mouse without MPTP. *=p<0.05, =p<0.01; *=p<0.005. N=6 per group.

Figure 4:
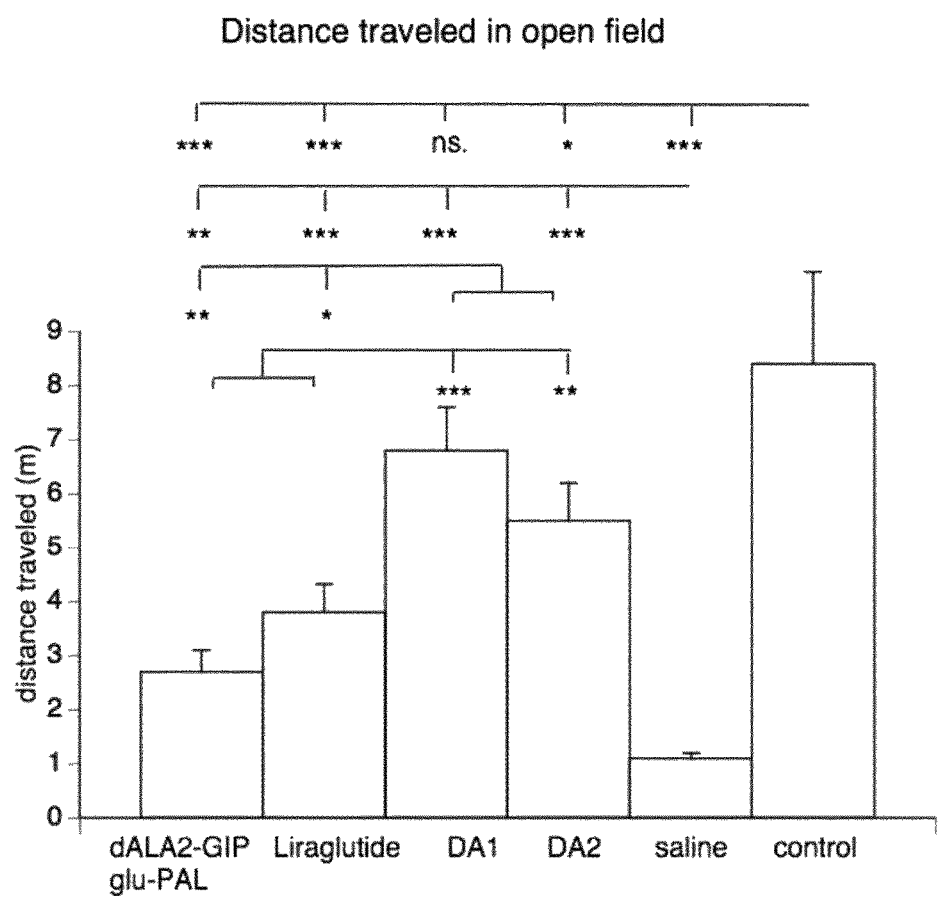

FIG. 4 illustrates that the DA1 (SEQ ID NO. 1) and DA2 (SEQ ID NO. 2) peptides protect mice from an impairment of motor activity induced by MPTP to reduce the levels of dopamine. Both co-agonist peptides of embodiments of the present invention were superior to the single GIP or GLP-1 analogues. *=p<0.05, =p<0.01; *=p<0.005. N=6 per group.

Figure 5:
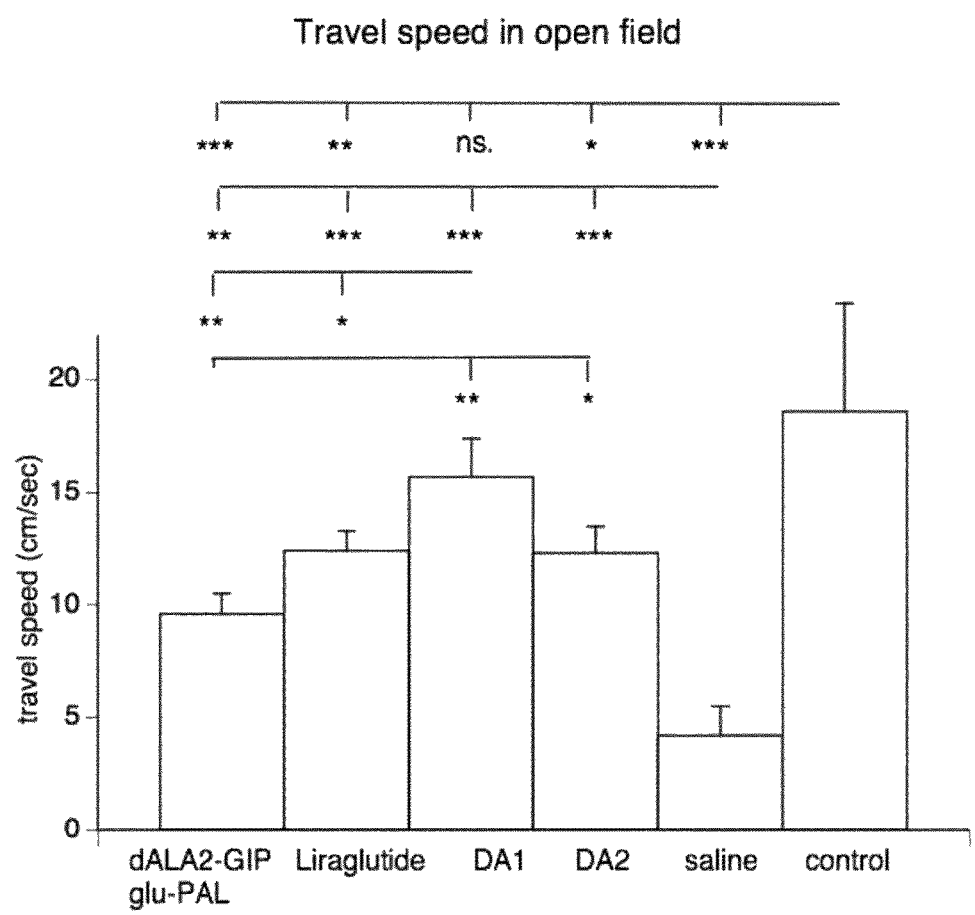

FIG. 5 is a graph illustrating that the peptides protect mice from an impairment of motor activity induced by MPTP to reduce the levels of dopamine. Open-field motor activity tasks were performed as described below. Both co-agonist peptides of embodiments of the present invention were superior to the single GIP or GLP-1 analogues. *=p<0.05, =p<0.01; *=p<0.005. N=6 per group.

Figure 6:
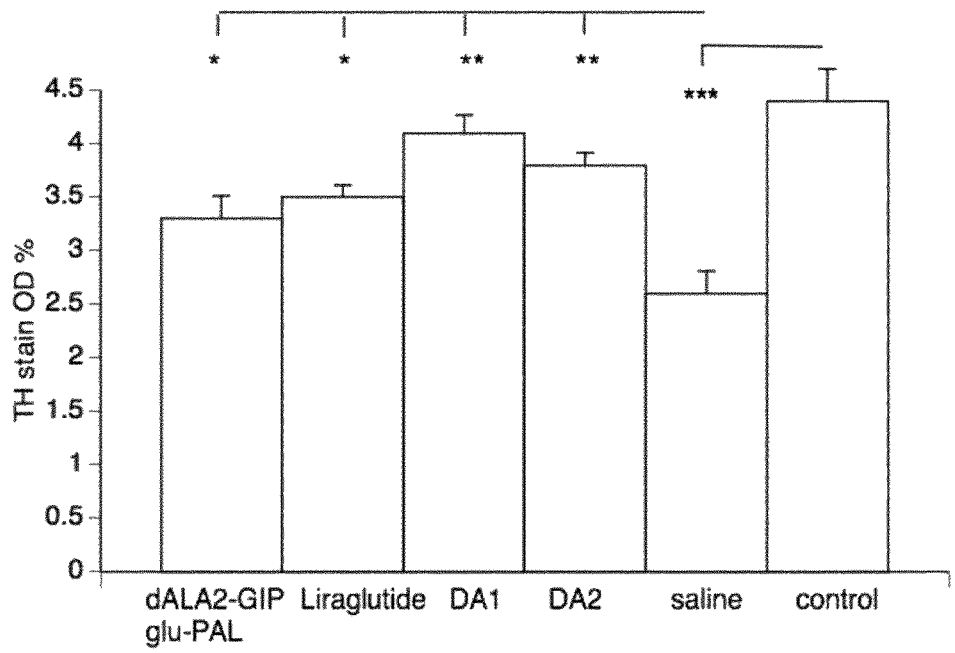

FIG. 6 illustrates MPTP-induced reduction of the enzyme TH that synthetises dopamine in the substantia nigra, pars compacta. A reduction is prevented by all peptides in the brain area sustantia nigra pars compacta. *=p<0.05, =p<0.01; *=p<0.005. N=6 per group.

Figure 7:
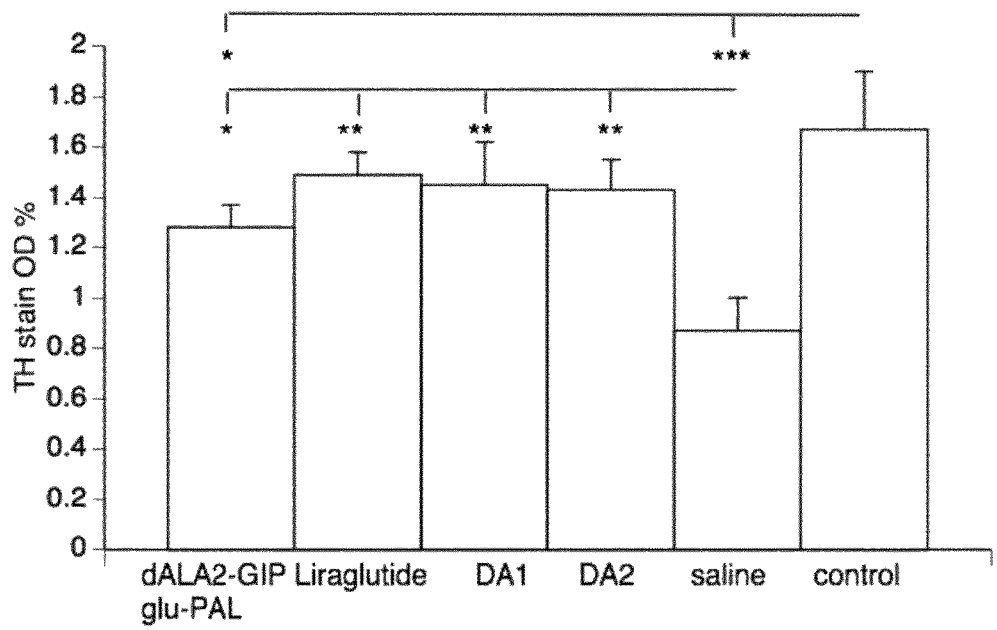

FIG. 7 is a graph illustrating MPTP-induced reduction of the enzyme TH that synthetises dopamine in the basal ganglia brain region. A reduction is prevented by all peptides in the striatum brain area. *=p<0.05, =p<0.01; *=p<0.005. N=6 per group.

FIG. 8 details amino acid sequences of peptides as described herein.

DETAILED DESCRIPTION

The practice of embodiments of the present invention will employ, unless otherwise indicated, conventional techniques of molecular biology, microbiology, recombinant DNA technology and immunology, which are within the skill of those working in the art.

Most general molecular biology, microbiology recombinant DNA technology and immunological techniques can be found in Sambrook et al, Molecular Cloning, A Laboratory Manual (2001) Cold Harbor-Laboratory Press, Cold Spring Harbor, N.Y. or Ausubel et al., Current protocols in molecular biology (1990) John Wiley and Sons, N.Y. Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, 2$^{nd}$ ed., 2002, CRC Press; The Dictionary of Cell and Molecular Biology, 3$^{rd}$ ed., Academic Press; and the Oxford University Press, provide a person skilled in the art with a general dictionary of many of the terms used in this disclosure.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The invention is not restricted to any details of any embodiments disclosed herein. The invention extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Units, prefixes and symbols are denoted in their Systéme International de Unitese (SI) accepted form. Numeric ranges are inclusive of the numbers defining the range. Unless other indicated, amino acid sequences are written left to right in amino to carboxy orientation. All amino acid residues in peptides of embodiments of the invention are preferably of the L-configuration. However, D-configuration amino acids may also be present.

The present disclosure relates to the use of GIP/GLP-1 co-agonist peptides. The native human GLP-1 peptide and GIP peptide sequences are known in the art. The term "GLP-1", or "hGLP-1" as used herein refers to the human Glucagon-Like Peptide-1 (GLP-1 (7-37)), the sequence of which is included herein as SEQ ID No. 8. The peptide having the sequence of SEQ ID No 8 may also be designated "native" GLP-1.

The *Homo sapiens* GLP-1(7-37) sequence is:

```
                                          [SEQ ID No. 8]
   HAEGTFTSDVSSYLEGQAAK EFIAWLVKGR G-OH
```

The term "GIP", or "hGIP" as used herein refers to the human Gastric Inhibitory Peptide (also known as glucose-dependent insulinotropic peptide) the sequence of which is included herein as SEQ. ID No. 9. The peptide having the sequence of SEQ. ID No. 9 may also be designated "native" GIP:

```
                                          [SEQ ID No. 9]
   YAEGTFISDYSIAMDKIHQQDFVNWLLAQKGKKNDWKHNITQ-OH
```

As used herein, a general reference to "GIP" or "GLP-1" in the absence of any further designation is intended to mean native GIP or native GLP-1, respectively.

As used herein, the term "peptide" encompasses a sequence of 3 or more amino acids and typically less than 50 amino acids, wherein the amino acids are naturally occurring or non-naturally occurring amino acids. Non-naturally occurring amino acids refer to amino acids that do not naturally occur in vivo but which, nevertheless, can be incorporated into the peptide structures described herein.

As used herein, the terms "polypeptide" and "protein" are terms that are used interchangeably to refer to a polymer of amino acids, without regard to the length of the polymer. Typically, polypeptides and proteins have a polymer length that is greater than that of "peptides."

As used herein an amino acid "modification" refers to a substitution, addition or deletion of an amino acid, and includes substitution with or addition of any of the 20 amino acids commonly found in human proteins, as well as atypical or non-naturally occurring amino acids. Throughout the application, all references to a particular amino acid position by number (e.g. position 28) refer to the amino acid at that position in the GIP/GLP-1 dual agonist of embodiments of the present invention.

Throughout this specification, the conventional one letter and three letter codes for naturally occurring amino acids are used, as well as generally accepted three letter codes for other amino acids, such as for example Aib (α-aminoisobutyric acid).

Thus, in an aspect of the present invention, there is provided a GIP/GLP-1 co-agonist peptide, or a derivative or a pharmaceutically acceptable salt or solvate of the peptide or the derivative, for use in the treatment and/or prophylaxis of a neurological disorder. Aptly, the co-agonist peptide has a GLP-1 percentage potency within about 10-fold of the GIP percentage potency.

As used herein, the term "agonist" refers to a substance (ligand) that activates the receptor type in question. The terms "dual agonist" and "co-agonist" are used herein are interchangeable and refer to a substance (ligand) that activate two receptor types. Aptly, the GIP/GLP-1 co-agonist peptides described herein have balanced activity at both the GLP-1R and the GIPR. In one embodiment, the co-agonist peptide has an $EC_{50}$ at the human GLP-1 receptor within about 10-fold of the $EC_{50}$ at the human GIP receptor. Activity in in vitro assays may be used as a measure of the peptides' activity.

Further embodiments of the invention are described herein.

In one aspect of the present invention, there is provided a GIP/GLP-1 co-agonist peptide or a pharmaceutically acceptable salt or solvate thereof for use in the treatment and/or prophylaxis of a neurological disorder, wherein the co-agonist peptide is represented by the general Formula I:

```
                                         [SEQ ID No. 12]
   Tyr-Aib-Glu-Gly-Thr-Phe-Thr-Ser-Asp-Tyr-Ser-Ile-

Tyr-Leu-Asp-Lys-Gln-Ala-Ala-Aib-Glu-Phe-Val-

Xaa24-Trp-Leu-Leu-Ala-Gly-Y1-R2  (I)
``` wherein $Xaa^{24}$ is selected from Asn and Cys;

Y1 is selected from absent or an extension comprising at least eight amino acid molecules; and $R^2$ is selected from —NH2 and —OH.

In one embodiment, the GIP-GLP-1 co-agonist peptide is an isolated peptide.

In one embodiment, $Xaa^{24}$ is Cys. In one embodiment, $Xaa^{24}$ is Asn.

Aptly, Y1 is an extension comprising at least 10 amino acids.

Aptly, Y1 is an extension comprising at least 11 amino acids.

Aptly, Y1 is selected from:

```
                                          [SEQ ID No. 3]
   Gly-Pro-Ser-Ser-Gly-Ala-Pro-Pro-Pro-Ser;

[SEQ ID No. 4]
   Gly-Pro-Ser-Ser-Gly-Ala-Pro-Pro-Pro-Ser-Lys;

[SEQ ID No. 5]
   Gly-Pro-Ser-Ser-Gly-Ala-Pro-Pro-Pro-Ser-Cys;

[SEQ ID No. 6]
   Pro-Ser-Ser-Gly-Ala-Pro-Pro-Pro-Ser;

[SEQ ID No. 7]
   Pro-Ser-Ser-Gly-Ala-Pro-Pro-Ser;
``` and absent.

Aptly, Y1 is Gly-Pro-Ser-Ser-Gly-Ala-Pro-Pro-Pro-Ser [SEQ ID No. 3].

In one embodiment, Y1 is Gly-Pro-Ser-Ser-Gly-Ala-Pro-Pro-Pro-Ser-Cys [SEQ ID No. 5].

In one embodiment, Y1 is Gly-Pro-Ser-Ser-Gly-Ala-Pro-Pro-Pro-Ser-Lys [SEQ ID No. 4].

In one embodiment, the carboxyl terminus of the peptide is amidated.

In one embodiment, the carboxyl terminus of the peptide is unmodified.

In one embodiment, the co-agonist peptide comprises a hydrophilic moiety covalently linked to an amino acid residue. Thus, in some embodiments, the co-agonist peptide comprises a hydrophilic moiety e.g. a hydrophilic polymeric moiety. One or more side chains of an amino acid residue in the peptide may be conjugated to the polymeric moiety, for example, in order to increase solubility and/or half-life in vivo (e.g. in plasma) and/or bioavailability. Such modification is also known to reduce clearance (e.g. renal clearance) of therapeutic proteins and peptides.

Aptly, the co-agonist peptide comprises a hydrophilic moiety covalently linked to an amino acid at position 24 ($Xaa^{24}$).

In one embodiment, the co-agonist peptide comprises a hydrophilic moiety covalently linked to an amino acid at position 39 or 40, when Y1 is an extension comprising at least 10 amino acids or at least eleven amino acids.

In one embodiment, $Xaa^{39}$ or $Xaa^{40}$ is Cys and the co-agonist peptide comprises a hydrophilic moiety covalently linked to Cys(39) or Cys(40).

Aptly, $Xaa^{24}$ is Cys and wherein the co-agonist peptide comprises a hydrophilic moiety covalently linked to Cys (24).

In one embodiment, the hydrophilic moiety is a polymeric moiety. In one embodiment, the polymeric moiety is a water-soluble polymer. The polymeric moiety is aptly water-soluble, non-toxic, and pharmaceutically inert.

Aptly, the water-soluble polymer is a polyethylene glycol and in some embodiments, the peptide is "pegylated". As used herein, the terms "pegylated" and "pegylation" have their general meaning in the art and refer generally, for example, to the process of chemically modifying a peptide as described herein by covalent attachment of one or more molecules of polyethylene glycol or a derivative thereof, such as by reacting a polyalkylene glycol, preferably an activated polyalkylene glycol, with a suitable reactive group or moiety such as an amino acid, e.g. lysine, to form a covalent bond.

Although "pegylation" is often carried out using polyethylene glycol or derivatives thereof, such as methoxy polyethylene glycol, the term as used herein also includes any other useful polyalkylene glycol, such as, for example polypropylene glycol. As used herein, the term "PEG" refers to polyethylene glycol and its derivatives as understood in the art (see for example U.S. Pat. Nos. 5,445,090, 5,900,461, 5,932,462, 6,436,386, 6,448,369, 6,437,025, 6,448,369, 6,495,659, 6,515,100, and 6,514,491).

The polymer used for pegylation can be of any molecular weight, and can be branched or unbranched. Aptly, the polyethylene glycol has a molecular weight between about 1000 Daltons and about 100,000 Da (the term "about" indicating that in preparations of polyethylene glycol, some molecules will weigh more, some less, than the stated molecular weight). For example, the polyethylene glycol can have an average molecular weight of about 1000, 5000, 10000, 15000, 20000, 25000, 30000, 35000, 40000, 50000, 60000, 70000, 80000, 90000 or 100000 Da.

Aptly, the PEG moiety can be covalently bound through amino acid residues via a reactive group, such as, a free amino, carboxyl group or sulfhydryl group. Reactive groups are those to which an activated PEG molecule can be bound. Examples of naturally occurring amino acid residues having a free amino group include lysine residues and the N-terminal amino acid residues; those having a free carboxyl group include aspartic acid residues glutamic acid residues and the C-terminal amino acid residue. Sulfhydryl groups (e.g., on cysteine) can also be used as a reactive group for attaching the polyethylene glycol molecules. PEG molecules may also be incorporated by conjugation to reactive functional groups introduced synthetically as unnatural amino acids or alternatively, PEG may be conjugated to the peptide using orthogonal methods during peptide synthesis.

One such strategy is to link a PEG to a cysteine residue that is part of the GIP/GLP-1 co-agonist peptide. Attachment to cysteine can be achieved using various approaches. One common method involves reacting a PEG-maleimide to the thiol group of cysteine. Another approach is to attach PEG to the carboxy-terminus of the peptide via enzymatic coupling (as described in for example U.S. Pat. No. 4,343,898).

The water soluble polymer, e.g. a PEG moiety, may be straight-chain or branched. It may have a molecular weight of 500-60,000 Da, for example 500-10,000 Da, 1000-5000 Da, 10,000-20,000 Da, or 20,000-60,000 Da. Aptly, the PEG has a molecular weight of approximately 40,000 Da.

The number of PEG moieties attached to each peptide (i.e., the degree of substitution) can also vary. For example, the peptide may be linked, on average, to 1, 2, 3, 4, or 5, or more polyethylene glycol molecules. Methods for determining the degree of substitution are discussed, for example, in Delgado et al., 1992, *Crit. Rev. Thera. Drug Carrier Sys.* 9:249-304.

In an embodiment, the water soluble polymer is a polyethylene glycol moiety having an average molecular weight of between about 20,000 Daltons and about 60,000 Daltons.

Aptly, the water soluble polymer is a polyethylene glycol moiety having a molecular weight of between about 35,000 Daltons and about 45,000 Daltons. Aptly, the water soluble polymer is a polyethylene glycol moiety having a molecular weight of approximately 40,000 Daltons.

In one embodiment, $Xaa^{24}$ is Cys and the co-agonist peptide comprises a PEG molecule having an average molecular weight of 40,000 Daltons covalently linked to Cys(24).

Other suitable polymeric moieties include poly-amino acids such as poly-lysine, poly-aspartic acid and poly-glutamic acid (see for example Gombotz, et al. (1995), *Bioconjugate Chem.*, vol. 6:332-351; Hudecz, et al. (1992), *Bioconjugate Chem.*, vol. 3, 49-57; Tuskada, et al. (1984), *J. Natl. Cancer Inst.*, vol 73: 721-729; and Pratesi, et al. (1985), *Br. J. Cancer*, vol. 52: 841-848).

In one embodiment, the peptide comprises a lipophilic substituent. Thus, in one embodiment, one or more of the amino acid side chains in the peptide may be conjugated to a lipophilic substituent. The lipophilic substituent may be covalently bonded to an atom in the amino acid side chain. In one embodiment, the lipophilic substituent may be conjugated to a side chain of an amino acid by a spacer. The term "conjugated" as used herein refers to a physical attachment of one identifiable moiety to another and the structural relationship between such moieties.

Without being bound by theory, in certain embodiments, it is understood that the lipophilic substituent binds albumin in the blood stream, therefore shielding the peptide of embodiments of the invention from enzymatic degradation and thereby enhancing the half-life of the peptide. It may also modulate the potency of the peptide.

The peptides as described herein may comprise one or more lipophilic substituents. If the peptide comprises more than one lipophilic substituent, they may be the same or different.

Aptly, the lipophilic substituent may include a hydrocarbon chain having 4 to 30 C atoms. Aptly, the lipophilic substituent comprises a hydrocarbon chain having 10 to 24 carbon (C) atoms.

In one embodiment, the peptide comprises a lipophilic substituent having at least 8 or 12 C atoms. Aptly, the lipophilic substituent has 24 C atoms or fewer. In one embodiment, the lipophilic substituent has 14 C atoms. In one embodiment, the lipophilic substituent has 16 C atoms.

The hydrocarbon chain may be linear or branched and may be saturated or unsaturated. Aptly, the hydrocarbon chain is substituted with a moiety which forms part of the attachment to the amino acid side chain or a spacer, for example an acyl group, a sulphonyl group, an N atom, an O atom or an S atom.

In one embodiment, the lipophilic substituent comprises an acyl group. In one embodiment, the lipophilic substituent is a fatty acid molecule. Aptly, the fatty acid molecule is selected from a C-8 octanoyl group, a C-10 decanoyl group, a C-12 lauroyl group, a C-14 myristoyl group, a C-16 palmitoyl group, a C-18 stearoyl group and a C-20 acyl group.

In one embodiment, the hydrocarbon chain has 16 C atoms and is saturated. In one embodiment, the lipophilic substituent is palmitate.

In one embodiment, the lipophilic substituent is conjugated to an amino acid side chain by a spacer. Aptly, when present, the spacer is attached to the lipophilic substituent and to the amino acid side chain. In one embodiment, the spacer is a natural or an unnatural amino acid. Alternatively, the spacer comprises a number of repeat units, each of which is a natural or an unnatural amino acid. Aptly, the spacer (or one or more of the repeat units of the spacer, if it has repeat units) is selected from Gly, Pro, Ala, Val, Leu, Ile, Met, Cys, Phe, Tyr, Trp, His, Lys, Arg, Gln, Asn, α-Glu, γ-Glu, Asp, Ser, Thr, Gaba, Aib, β-Ala, 5-aminopentanoyl, 6-aminohexanoyl, 7-aminoheptanoyl, 8-aminooctanoyl, 9-aminononanoyl, 10-aminodecanoy and 8-amino-3,6-dioxaoctanoyl.

In one embodiment, the spacer is gamma glutamine (γ-Glu).

Aptly, the lipophilic substituent is conjugated to any amino acid side chain in the peptide of embodiments of the present invention. Aptly, the amino acid side chain includes a carboxyl, hydroxyl, thiol, amide or amine group, for forming an ester, a sulphonyl ester, a thioester, an amide or a sulphonamide with the spacer or the lipophilic substituent. For example, the lipophilic substituent or the spacer may be conjugated to Asn, Asp, Glu, Gln, His, Lys, Arg, Ser, Thr, Tyr, Trp or Cys of the peptide.

Aptly, the peptide comprises a lipophilic substituent which is a C16 saturated fatty acid moiety conjugated to the peptide by a γ-Glu spacer. Aptly, the γ-Glu spacer is conjugated to a Lys amino acid residue at the carboxyl terminus of the peptide.

In an alternative embodiment, the peptide comprises a C16 saturated fatty acid moiety covalently bonded to a Lys amino acid residue at the carboxyl terminus of the peptide.

In one embodiment, the co-agonist peptide comprises a spacer which conjugates the lipophilic substituent to an amino acid of the peptide. Aptly, the spacer is a residue from a naturally occurring or unnatural amino acid.

In one embodiment, the co-agonist peptide further comprises one or more conservative amino acid substitutions. As used herein an amino acid "substitution" refers to the replacement of one amino acid residue by a different amino acid residue. As used herein, the term "conservative amino acid substitution" is defined herein as exchanges within one of the following five groups:

I. Small Aliphatic, Nonpolar or Slightly Polar Residues:
   Ala, Ser, Thr, Pro, Gly;
II. Polar, Negatively Charged Residues and their Amides and Esters:
   Asp, Asn, Glu, Gln, cysteic acid and homocysteic acid;
III. Polar, Positively Charged Residues:
   His, Arg, Lys; Ornithine (Orn)
IV. Large, Aliphatic, Nonpolar Residues:
   Met, Leu, Ile, Val, Cys, Norleucine (Nle), homocysteine
V. Large, Aromatic Residues:
   Phe, Tyr, Trp, acetyl phenylalanine In an embodiment, the co-agonist peptide comprises the following amino acid sequence:

[SEQ ID No. 1]
YXEGTFTSDYSIYLDKQAAXEFVNWLLAGGPSSGAPPP

S[Lys-C16]-NH2 wherein C16 is a saturated fatty acid, wherein optionally C16 is palmitate and wherein X is amino-isobutyric acid. Aptly, the carboxyl terminus is amidated.

In an embodiment, the co-agonist peptide consists of the following amino acid sequence:

[SEQ ID No. 1]
YXEGTFTSDYSIYLDKQAAXEFVNWLLAGGPSSGAPPP

S[Lys-C16]-NH2 wherein C16 is a saturated fatty acid, wherein optionally C16 is palmitate and further wherein X is amino-isobutyric acid. Aptly, the peptide does not comprise a linker between the fatty acid and the C-terminus amino acid (Lys) of the peptide. Aptly, the carboxyl terminus is amidated.

In one embodiment, the co-agonist peptide comprises the following amino acid sequence:

[SEQ ID No. 2]
YXEGTFTSDYSIYLDKQAAXEFV[Cys-40 kDaPEG]WLLAGGPSSGA

PPPS[Lys-γE-C16]-NH2 wherein C16 is a saturated fatty acid, wherein optionally C16 is palmitate and wherein X is amino-isobutyric acid. Aptly, the peptide comprises a PEG molecule having an average molecular weight of 40 kDa covalently linked to Cys24. Aptly, the peptide comprises a gamma-glutamate linker between the C-terminal amino acid of the peptide and the fatty acid. Aptly, the carboxyl terminus is amidated.

In one embodiment, the co-agonist peptide consists of the following amino acid sequence:

[SEQ ID No. 2]
YXEGTFTSDYSIYLDKQAAXEFV[Cys-40 kDaPEG]WLLAGGPSSGA

PPPS[Lys-γE-C16]-NH2 wherein C16 is a saturated fatty acid, wherein optionally C16 is palmitate and wherein X is amino-isobutyric acid. Aptly, the peptide comprises a PEG molecule having an average molecular weight of 40 kDa covalently linked to Cys24. Aptly, the peptide comprises a gamma-glutamate linker between the C-terminal amino acid of the peptide and the fatty acid. Aptly, the carboxyl terminus is amidated.

In one embodiment, the co-agonist peptide is for use to attenuate long term potentiation (LTP) of synaptic transmission.

In one embodiment, the co-agonist peptide is for use in the treatment of a neurological disorder which is caused by or associated with beta-amyloid protein plaque deposition in an area of the patient. Aptly, the beta-amyloid plaque deposition is in the brain of the patient.

In one embodiment, the co-agonist peptide is for use in the treatment and/or prophylaxis of a neurological disorder caused by, or associated with, dysfunction of long-term potentiation of synaptic transmission.

In one embodiment, the co-agonist peptide is for use in the treatment and/or prophylaxis of a neurological disorder caused by, or associated with, inflammation.

In one embodiment, the co-agonist peptide is for use in the treatment of a neurological disorder associated with motor impairment.

In one embodiment, the co-agonist peptide is for use in the treatment and/or prophylaxis of a neurological disorder affecting cognitive function, e.g. dementia, stroke, schizophrenia and/or bipolar disorder.

In one embodiment, the co-agonist peptide is for the treatment of cerebral ischemia associated with stroke.

In one embodiment, the co-agonist peptide is for use in the treatment and/or prophylaxis of a disorder selected from post-traumatic stress disorder, epilepsy, Tourette's syndrome, and hallucinations; and dysfunctional cognitive processes, optionally selected from attention, calculation, memory, judgment, insight, learning and reasoning.

In one embodiment, the co-agonist peptide is for use in the treatment and/or prophylaxis of a neurodegenerative disorder e.g. Alzheimer's disease, Parkinson's disease, Amyotrophic Lateral Sclerosis, peripheral neuropathy, Huntington's disease and Creutzfeldt-Jacob disease.

In one embodiment, the co-agonist peptide is for use in the treatment and/or prophylaxis of multiple sclerosis.

In one embodiment, the co-agonist peptide is for use in the treatment and/or prophylaxis of a neurological disorder selected from clinical or pre-clinical Alzheimer's disease, prodromal Alzheimers disease, and clinical or preclinical amyloid angiopathy (CAA).

In one embodiment, the co-agonist peptide is for use in the treatment and/or prophylaxis of clinical Alzheimer's disease.

In one embodiment, the co-agonist peptide is for use in the treatment and/or prophylaxis of Parkinson's disease.

In a further aspect of the present invention, there is provided a method of treating and/or lessening the likelihood of occurrence, or even preventing a neurological disorder comprising administering to a patient in need thereof a pharmaceutical composition comprising a GIP/GLP-1 co-agonist peptide, or a derivative or a pharmaceutically acceptable salt or solvate of the peptide or the derivative, wherein said co-agonist peptide is represented by the general Formula I;

[SEQ ID No. 12]
Tyr-Aib-Glu-Gly-Thr-Phe-Thr-Ser-Asp-Tyr-Ser-Ile-

Tyr-Leu-Asp-Lys-Gln-Ala-Ala-Aib-Glu-Phe-Val-Xaa$^{24}$-

Trp-Leu-Leu-Ala-Gly-Y1-R$^2$ (I)

wherein

Xaa$^{24}$ is selected from Asn and Cys;

Y1 is selected from absent or an extension comprising at least nine amino acid molecules; and R$^2$ is selected from —NH2 and —OH.

In one embodiment, the method comprises administering a co-agonist peptide as described herein.

Aptly, the co-agonist peptide comprises the following sequence:

[SEQ ID No. 1]
YXEGTFTSDYSIYLDKQAAXEFVNWLLAGGPSSGAPPP

S[Lys-C16]-NH2, wherein C16 is a saturated fatty acid. Aptly, C16 is palmitate. Aptly, X is amino-isobutyric acid. Aptly, the peptide does not comprise a linker between the fatty acid and the C-terminus amino acid of the peptide. X is amino-isobutyric acid.

Aptly, the peptide comprises the following sequence:

[SEQ ID. No. 2]
YXEGTFTSDYSIYLDKQAAXEFV[Cys-40 kDaPEG]WLLAGGPSSGAP

PPS[Lys-γE-C16]-NH2 wherein C16 is a saturated fatty acid. Aptly, C16 is palmitate. Aptly, X is amino-isobutyric acid.

Aptly, the peptide comprises a PEG molecule having an average molecular weight of 40 kDa covalently linked to Cys24. Aptly, the peptide comprises a gamma-glutamate linker between the C-terminal amino acid of the peptide and the fatty acid.

In one embodiment, the method is for the treatment of a neurological disorder selected from post-traumatic stress disorder, epilepsy, Tourette's syndrome, and hallucinations; and dysfunctional cognitive processes. Aptly, the disorder is a dysfunctional cognitive process selected from attention, calculation, memory, judgment, insight, learning and reasoning.

In one embodiment, the method is a method of treating and/or lessening the likelihood of occurrence, or even preventing a neurodegenerative disorder. Aptly, the neurodegenerative disorder is selected from Alzheimer's Disease, Parkinson's Disease, Huntington's disease, Amyotrophic Lateral Sclerosis, peripheral neuropathy, and Creutzfeldt-Jacob disease.

In one embodiment, the method is a method of treating and/or lessening the likelihood of occurrence, or even preventing a neurological disorder selected from clinical or pre-clinical Alzheimer's disease, prodromal Alzheimer's disease, and clinical or preclinical amyloid angiopathy (CAA).

In one embodiment, the method is for the treatment and/or lessening the likelihood of occurrence, or even prevention of clinical Alzheimer's disease. In one embodiment, the method is for the treatment and/or lessening the likelihood of occurrence of Parkinson's Disease.

In one embodiment, the method is a method of lessening the likelihood of occurrence, or even preventing and/or treating stroke. Aptly, the method is a method of lessening the likelihood of occurrence, or even preventing and/or treating cerebral ischemia associated with stroke.

In one embodiment, the method is a method of lessening the likelihood of occurrence, or even preventing and/or treating multiple sclerosis.

In a further aspect of the present invention, there is provided a GIP/GLP-1 co-agonist peptide for use in the treatment and/or prophylaxis of clinical Alzheimer's disease, comprising the following sequence:

[SEQ ID No. 1]
YXEGTFTSDYSIYLDKQAAXEFVNWLLAGGPSSGAPPP

S[Lys-C16]-NH2, wherein C16 is a saturated fatty acid. Aptly, C16 is palmitate. Aptly, X is amino-isobutyric acid.

In a further aspect of the present invention, there is provided a GIP/GLP-1 co-agonist peptide for use in the treatment and/or prophylaxis of clinical Alzheimer's disease, wherein the peptide consists of the following sequence:

[SEQ ID No. 1]
YXEGTFTSDYSIYLDKQAAXEFVNWLLAGGPSSGAPPP

S[Lys-C16]-NH2, wherein C16 is a saturated fatty acid. Aptly, C16 is palmitate. Aptly, X is amino-isobutyric acid.

In a further aspect of the present invention, there is provided a peptide for use in the treatment and/or prophylaxis of clinical Alzheimer's disease, comprising the following sequence:

[SEQ ID No. 2]
YXEGTFTSDYSIYLDKQAAXEFV[Cys-40 kDaPEG]WLLAGGPSSGA

PPPS[Lys-γE-C16]-NH2, wherein C16 is a saturated fatty acid. In one embodiment, C16 is palmitate. Aptly, X is amino-isobutyric acid. Aptly, the peptide comprises a PEG molecule having an average molecular weight of 40 kDa covalently linked to Cys24. Aptly, the peptide comprises a gamma-glutamate linker between the C-terminal amino acid of the peptide and the fatty acid.

In one embodiment, 40 kDaPEG is a PEG molecule having a MW of 40 kDa.

In a further aspect of the present invention, there is provided a peptide for use in the treatment and/or prophylaxis of clinical Alzheimer's disease, wherein the peptide consists of the following sequence:

[SEQ ID No. 2]
YXEGTFTSDYSIYLDKQAAXEFV[Cys-40 kDaPEG]WLLAGGPSSGA

PPPS[Lys-γE-C16]-NH2, wherein C16 is a saturated fatty acid. In one embodiment, C16 is palmitate. Aptly, X is amino-isobutyric acid. Aptly, the peptide comprises a PEG molecule having an average molecular weight of 40 kDa covalently linked to Cys24. Aptly, the peptide comprises a gamma-glutamate linker between the C-terminal amino acid of the peptide and the fatty acid.

In a further aspect of the present invention, there is provided a GIP/GLP-1 co-agonist peptide for use in the treatment and/or prophylaxis of Parkinson's disease, comprising the following sequence:

[SEQ ID No. 1]
YXEGTFTSDYSIYLDKQAAXEFVNWLLAGGPSSGAPPP

S[Lys-C16]-NH2, wherein C16 is a saturated fatty acid. Aptly, C16 is palmitate. Aptly, X is amino-isobutyric acid.

In a further aspect of the present invention, there is provided a GIP/GLP-1 co-agonist peptide for use in the treatment and/or prophylaxis of Parkinson's disease, wherein the peptide consists of the following sequence:

[SEQ ID No. 1]
YXEGTFTSDYSIYLDKQAAXEFVNWLLAGGPSSGAPPP

S[Lys-C16]-NH2, wherein C16 is a saturated fatty acid. Aptly, C16 is palmitate. Aptly, X is amino-isobutyric acid.

In a further aspect of the present invention, there is provided a GIP/GLP-1 co-agonist peptide for use in the treatment and/or prophylaxis of Parkinson's disease, comprising the following sequence:

[SEQ ID No. 2]
YXEGTFTSDYSIYLDKQAAXEFV[Cys-40 kDaPEG]WLLAGGPSSGA

PPPS[Lys-γE-C16]-NH2, wherein C16 is a saturated fatty acid and wherein optionally C16 is palmitate. Aptly, 40 kDa PEG is a PEG molecule having a molecular weight of 40 kDa. Aptly, X is amino-isobutyric acid.

In a further aspect of the present invention, there is provided a GIP/GLP-1 co-agonist peptide for use in the treatment and/or prophylaxis of Parkinson's disease, wherein the peptide consists of the following sequence:

[SEQ ID No. 2]
YXEGTFTSDYSIYLDKQAAXEFV[Cys-40 kDaPEG]WLLAGGPSSGA

PPPS[Lys-γE-C16]-NH2, wherein C16 is a saturated fatty acid and wherein optionally C16 is palmitate. Aptly, X is amino-isobutyric acid. Aptly, the peptide comprises a PEG molecule having an average molecular weight of 40 kDa covalently linked to Cys24. Aptly, the peptide comprises a gamma-glutamate linker between the C-terminal amino acid (Lys) of the peptide and the fatty acid.

The peptides of embodiments of the present invention may be manufactured either by standard synthetic methods, recombinant expression systems, or any other state of the art method. Thus the GIP/GLP-1 co-agonists as described herein may be synthesized in a number of ways, including, for example, a method which comprises:

(a) synthesizing the peptide by means of solid-phase or liquid-phase methodology, either stepwise or by fragment assembly, and isolation and purifying of the final peptide product; or (b) expressing a nucleic acid construct that encodes the peptide in a host cell, and recovering the expression product from the host cell or culture medium; or (c) effecting cell-free in vitro expression of a nucleic acid construct that encodes the peptide, and recovering the expression product;

or any combination of methods of (a), (b), and (c) to obtain fragments of the peptide, subsequently ligating the fragments to obtain the peptide, and recovering the peptide.

Aptly, the peptides described herein are synthesized by means of solid-phase or liquid-phase peptide synthesis, as described in for example WO98/11125. Aptly, the peptides may be synthesized as described in Finan et al. (*Sci. Transl. Med.* 5 209ra151 (2013) pp 1 to 16).

The peptides of the present disclosure may be formulated as pharmaceutical compositions prepared for storage or administration for use in the treatment and/or lessening the likelihood of occurrence, or even prevention of a neurological disorder as described herein. Such a composition typically comprises a therapeutically effective amount of a GIP/GLP-1 co-agonist peptide, in the appropriate form, in a pharmaceutically acceptable carrier.

The therapeutically effective amount of a GIP/GLP-1 co-agonist peptide as described herein will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The peptides of the present disclosure may be particularly useful for treatment of humans.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the person skilled in the art.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, arginine, lysine, or acetate or mixtures thereof. The term further encompasses any agents listed in the US Pharmacopeia for use in animals, including humans.

The term "pharmaceutically acceptable salt" refers to a salt of any one of the GIP/GLP-1 co-agonist peptide of embodiments of the invention. Salts include pharmaceutically acceptable salts such as acid addition salts and basic salts. Examples of acid addition salts include hydrochloride salts, citrate salts and acetate salts. Examples of basis salts include salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", $17^{th}$ edition. Ed. Alfonoso R. Gennaro (Ed.), Mark Publishing Company, Easton, Pa., U.S.A., 1985 and more recent editions, and in the Encyclopaedia of Pharmaceutical Technology.

The term "solvate" in the context of the present disclosure refers to a complex of defined stoichiometry formed between a solute (e.g., a peptide or pharmaceutically acceptable salt thereof according to the present disclosure) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

"Treatment" is an approach for obtaining beneficial or desired clinical results. For the purposes of the present disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of lessening the likelihood of occurrence, or even preventing the development or altering the pathology of a disorder. Accordingly, "treatment" refers to both therapeutic treatment and prophylactic or preventative measures in certain embodiments. Those in need of treatment include those already with the disorder as well as those in which the likelihood of occurrence of the disorder is to be lessened or even prevented. By treatment is meant inhibiting or reducing an increase in pathology or symptoms when compared to the absence of treatment, and is not necessarily meant to imply complete cessation of the relevant condition.

The pharmaceutical compositions for use in the treatment of a neurological disorder can be in unit dosage form. In such form, the composition is divided into unit doses containing appropriate quantities of the active component. the unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. In certain embodiments, packaged forms include a label or insert with instructions for use. Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, and transdermal) administration. The formulations may conveniently be presented in unit dosage form and may be prepared by any of the methods well known in the art of pharmacy.

As used herein an "effective" amount or a "therapeutically effective amount" of a peptide refers to a nontoxic but sufficient amount of the peptide to provide the desired effect. The amount that is "effective" will vary from subject to subject, depending on the age and general condition of the individual, mode of administration, and the like. An appropriate "effective" amount in any individual case may be determined by one of ordinary skill in the art using routine experimentation.

The terms "patient", "subject" and "individual" may be used interchangeably and refer to either a humans or non-human mammal. Aptly, the subject is a human.

The peptides described herein may be used to treat and/or lessen the likelihood of occurrence, or even prevent a neurological disorder e.g. a neurodegenerative disorder. In one embodiment, the peptide is for use in the treatment and/o lessening the likelihood of occurrence, or even prevention of Alzheimer's disease. Alzheimer's disease (AD) is a neurodegenerative disorder that results in the loss of cortical neurons, especially in the associative neocortex and hippocampus which in turn leads to slow and progressive loss of cognitive functions, ultimately leading to dementia and death. Major hallmarks of the disease are aggregation and deposition of misfolded proteins such as aggregated beta-amyloid peptide as extracellular senile or neuritic 'plaques', and hyperphosphorylated tau protein as intracellular neurofibrillary 'tangles' (NFTs).

Genetically, AD is divided into two forms: (1) early-onset familial AD (<60 years), and (2) late-onset sporadic AD (>60 years). Rare, disease causing mutations in Amyloid precursor protein (APP), Presenilin 1 (PSEN1), and Presenilin 2 (PSEN2) genes are known to result in early-onset familial AD while, APOE (allele 4) is the single most important risk factor for late-onset AD.

Although Alzheimer's disease develops differently for every individual, there are many common symptoms. Early symptoms are often mistakenly thought to be 'age-related' concerns, or manifestations of stress. In the early stages, the most common symptom is difficulty in remembering recent events. When AD is suspected, the diagnosis is usually confirmed with tests that evaluate behaviour and thinking abilities, often followed by a brain scan if available, however, examination of brain tissue is required for a definitive diagnosis.

As the disease advances, symptoms can include confusion, irritability, aggression, mood swings, trouble with language, and long-term memory loss. As the sufferer declines they often withdraw from family and society. Gradually, bodily functions are lost, ultimately leading to death. Since the disease is different for each individual, predicting how it will affect the person is difficult. AD develops for an unknown and variable amount of time before becoming fully apparent, and it can progress undiagnosed for years. On average, the life expectancy following diagnosis is approximately seven years. Fewer than three percent of individuals live more than fourteen years after diagnosis.

In one embodiment, the co-agonist peptide is for use in treating Alzheimer's disease. The peptide may be used to slow down and/or halt the progression of Alzheimer's disease in a subject. The peptide may be for use to slow down and/or lessen the likelihood of occurrence, or even prevent the progression to clinical Alzheimer's disease of a subject suffering from pre-clinical Alzheimer's Disease.

In one embodiment, the co-agonist peptide is for use in the treatment and/or lessening the likelihood of occurrence, or even prevention of Parkinson's disease. Parkinson's disease is a neurodegenerative disorder characterized by progressive neuronal loss, in particular of dopaminergic neurons of the substantia nigra, leading to motor disturbances such as tremor, rigidity, slowness of movement, and postural instability. In one embodiment, the peptide is for use to reduce and/or lessen the likelihood of occurrence, or even prevent motor disturbances associated with Parkinson's disease.

In addition, there is an increasing number of atypical Parkinson syndromes and subclasses of Parkinson's disease, which are associated with learning and memory deficits. Typical examples are Parkinson's Disease Dementia (PDD), Lewy Body Dementia (LBD) and Multi-Systems Atrophy (MSA). The peptide may be for use in the retrieval or improvement of learning processes or learning deficits and/ or the lessening of the likelihood of occurrence, or even prevention, retrieval or improvement of memory loss or memory impairment in a subject suffering from Parkinson's disease.

As noted above, the peptides disclosed herein may be for use in the treatment of other degenerative disorders e.g. stroke or multiple sclerosis.

EXAMPLES

Peptide Synthesis

Peptides were synthesized by GL Biochem Ltd. (Shanghai). The purity of the peptide was analysed by reversed-phase HPLC and characterised using matrix assisted laser desorption/ionisation time of flight (MALDI-TOF) mass spectrometry, with a purity >99%.

Peptides were reconstituted in Ultrapure® water to a concentration of 1 mg/ml in polypropylene tubes and frozen in aliquots to permit fresh preparation of doses required for injection.

The peptides tested were:

1. Liraglutide (SEQ ID No. 10) (GLP-1 analogue)—

Liraglutide (SEQ ID No. 10) is a peptide drug which is typically administered parenterally. Liraglutide (SEQ ID No. 10) is authorised for the treatment of Type 2 diabetes. Liraglutide (SEQ ID No. 10) is disclosed in WO98/08871 A1, Example 37. The amino acid sequence of liraglutide is shown in SEQ ID No. 10.

As shown in FIG. 10, the fatty acid is linked to amino acid Lys at position 26. The amino acid Lys at position 34 has been replaced by amino acid Arg.

2. DAla$^2$GIP-Lys$^{37}$-γ-Glu-PAL (SEQ ID No. 11)

The sequence of DAla$^2$GIP-Lys$^{37}$-γ-Glu-PAL is shown in FIG. 8 as SEQ. ID. No. 11.

Liraglutide (SEQ ID No. 10) is a GLP-1 agonist, whilst DAla$^2$GIP-Lys$^{37}$-γ-Glu-PAL is a GIP agonist.

3. A peptide referred to herein as DA1 (SEQ ID NO. 1) which has the following amino acid sequence:

```
                                          [SEQ ID No. 1]
YXEGTFTSDYSIYLDKQAAXEFVNWLLAGGPSSGAPPP

S[Lys-C16]-NH2
```

X=amino-isobutyric acid

The DA1 (SEQ ID NO. 1) peptide is a GLP-1/GIP dual agonist and is disclosed in Finan et al, 2013. The DA1 (SEQ ID NO. 1) peptide comprises a C16 fatty acid moiety (C:D: 16:0) attached to its C-terminal.

4. A peptide referred to herein as DA2 (SEQ ID No. 2) which has the following amino acid sequence:

```
                                          [SEQ ID No. 2]
YXEGTFTSDYSIYLDKQAAXEFV[Cys-40 kDAPEG]WLLAGGPSSGA

PPPS[Lys-γE-C16]-NH2
```

X=amino-isobutyric acid

DA2 (SEQ ID NO. 2) is a pegylated version of the DA1 (SEQ ID NO. 1) peptide in which the amino acid at position 24 has been modified to cysteine. DA2 (SEQ ID NO. 2) also comprises a spacer (γ-Glu) for linking the C16 fatty acid.

The DA1 (SEQ ID NO. 1) and DA2 (SEQ ID NO. 2) peptides have been characterised in cell culture and in animal models of diabetes. DA2 (SEQ ID NO. 2) also has been tested in patients with diabetes. The double agonists have superior effects in diabetes compared to single GLP-1 analogues (Finan et al., 2013). Details of the spacer of the DA2 (SEQ ID NO. 2) peptide and other spacers which are encompassed by embodiments of the present invention are provided in Madsen et al; Journal of Medicinal Chemistry, 2007, 50, (24), 6126-6132.

Transgenic Alzheimer's Disease Mouse Model

Animal models have been developed to test novel drugs. A standard model for Alzheimer's disease is transgenic mice that express human mutated genes for amyloid production that are known to induce Alzheimer's disease in humans. These APP/PS1 transgenic mice recapitulate some of the symptoms of Alzheimer's disease such as the aggregation of amyloid in the brain, memory loss and the loss of synapses (Radde et al., 2006).

The APP/PS1 mice express human Swedish mutated APP and human mutated presenilin-1 which induce Alzheimer's Disease in humans.

The dose of peptide tested was 25 nmol/kg body weight. The peptides were administered by a once-daily intraperitoneal injection for 8 weeks. Saline injections were administered as a control. Five animals per group were injected with a peptide or a saline control.

Brain Tissue Analysis for Amyloid Plaques and Synapse Numbers in AD Mice

Animals (5 per group) were perfused transcardially with 30 ml of ice-cold PBS and 30 ml of ice-cold 4% paraformaldehyde to postfix the brain. The brains were removed and placed in fresh 30% sucrose solution in PBS to cryoprotect tissue and cut at a thickness of 40 µm on a cryostat. Sections were chosen according to stereological rules, with the first section taken at random and every 5th section afterwards. Between 7 and 13 sections were analysed per brain.

Immunostaining techniques were used to assess the neuronal plaque load (anti beta-amyloid rabbit polyclonal antibody (1:200, rabbit polyclonal-Invitrogen 71-5800) and of synaptophysin (polyclonal rabbit anti-synaptophysin primary antibody, 1:2000, Abcam, Cambridge, UK) to measure the amount of synapses in the cortex. Brain samples were first exposed to 99% formic acid for 7 minutes and then washed 3 times for 10 minutes in TBS. Pre-treatment with 99% formic acid is known to drastically increase the detection of beta-Amyloid in formalin-fixed brain samples. Then samples were incubated in 0.3% $H_2O_2$ (Sigma Aldrich; Cat.-No.: 516813) in TBS for 30 minutes on the shaker to deplete endogenous peroxides activity, and were 3 times washed in TBS for 10 minutes afterwards.

To increase permeability of membranes in the brain tissue, samples were exposed to 0.3% Triton X-100 (Sigma Aldrich; Cat.-No.: 516813) in TBS for 10 minutes on the shaker. Unspecific proteinophilic binding in the tissue was saturated by incubating the samples with 5% goat serum (Gibco; Cat.-No.: 16210-064) in TBS for 30 minutes on the shaker.

A primary antibody against beta-Amyloid or synaptophysin was added and incubated overnight on the shaker at 4° C. The antibody was polyclonal and raised against a synthetic beta-Amyloid 1-43 peptide in rabbit. The primary antibody was used in a final dilution of 1 to 250 in TBS containing 2% goat serum and 10% Triton X-100. Afterwards, the samples were washed with TBS 3 times for 10 minutes and a secondary antibody was added for 90 minutes on the shaker at 4° C. The secondary antibody was a biotinylated anti-rabbit IgG raised in goat (Vectastain ABC Kit, Rabbit IgG; Vector Laboratories; Cat.-No.: PK-6101), and was used in a final dilution of 1 to 60 in TBS containing 1% goat serum and 10% Triton-X-100.

After washing 3 times for 10 minutes in TBS, samples were incubated in TBS containing 3% avidin solution (Vectastain ABC Kit, Rabbit IgG; Vector Laboratories; Cat.-No.: PK-6101) and 3% biotinylated horseradish peroxidase solution (Vectastain ABC Kit, Rabbit IgG; Vector Laboratories; Cat.-No.: PK-6101) for 90 minutes at 4° C. on the shaker. The samples were then washed 3 times in TBS for 10 minutes and then stained by adding phosphate-buffered saline containing 3% SG blue solution (SG Blue Peroxidase Kit; Vector Laboratories; Cat.-No.: SK-4700) and 3% $H_2O_2$ solution for 5 minutes and then again washed 3 times for 10 minutes with phosphate-buffered saline.

To enhance staining, samples were incubated with dd$H_2O$ containing 0.5% $CuSO_4$ (w/w) for 5 minutes. After washing 3 times for 10 minutes in dd$H_2O$, the brain slices were put onto silane-coated glass slides with a fine brush where they could dry overnight. Finally the slides were cover slipped with an aquatic mounting medium (VectaMountAQ Mounting Medium; Vector Laboratories, Cat.-No.: H-5501). As control served a set of samples from a 17 month old non-transgenic littermate processed together with the experimental samples.

Sections photographed under a microscope (Zeiss, Germany), randomised inbiased dissectors were overlain on to the brain section images and analysed using a Multi threshold plug-in with the software Image J (NIH, USA). Data were analysed using a one-way ANOVA with post-hoc Bonferroni tests.

Parkinson Mouse Model

A standard model to induce Parkinson like symptoms in mice is the injection of the chemical (MPTP) (Li et al., 2009). This chemical impairs or kills neurons in the brain that produce dopamine. The mice develop motor impairments, and the dopaminergic neurons in the brain are reduced in numbers and function. The enzyme tyrosine hydroxylase (TH) is required to synthetise dopamine. A loss of TH signifies a loss of dopamine production (Harkavyi et al., 2008).

Adult male C57BL/6 mice were given the dopaminergic toxin MPTP (20 mg/kg in 0.1 mL of PBS i.p. at 2-h intervals of 4 doses MPTP; Sigma) or vehicle (PBS). This treatment selectively affects dopaminergic neurons and induces Parkinson-like symptoms in mice. One group did not receive MPTP as a non-lesioned control.

The dose of peptide tested was 25 nmol/kg body weight. The peptides were administered by a once-daily intraperitoneal injection for 8 weeks. Saline injections were administered as a control. Five animals per group were injected with a peptide or a saline control.

Rotarod Motor Control Test

The rotarod consists of a rotating pole that accelerates over time. Mice are placed on the rod, and motor skills are tested by accelerating the rotation. As the rotation increases, animals lose grip and fall on a cushion located below the rod. Mice were given three trials with 45 min intertrial intervals on each of 2 consecutive days for 3 weeks. Each animal's endurance time was recorded, and the average was calculated. Data were analysed using a one-way ANOVA with post-hoc Bonferroni tests.

Open-Field Motor Activity Task

Mice (6 per group) received a session of 5 min in the empty open-field (58 cm in diameter; 35 cm high walls) with painted grey walls and grey floor. The movements and speed were tracked with a computerised video capture system and analysis software (Biosignals inc., New York, USA). Motor activity was recorded by total path length and travel speed. Data were analysed using two-way ANOVA with post-hoc tests.

Immunohistochemistry for TH in the Substantia Nigra Pars Compacta and the Striatum Six animals per group were analysed for expression of tyrosine hydroxylase (TH), a marker for dopamine production. Coronal brain sections (20 µm) from striatum (bregma 11 to 10.2) and SNpc (bregma 24.80 to 26.04) were analysed by immunohistochemistry using antibodies recognising TH.

Sections were cut on a cryostat and postfixed in 4% paraformaldehyde, washed in PBS, treated with 0.3% $H_2O_2$ in methanol for 20 min, and washed again. Incubation with TH (1:800) antibody was at 48 C overnight in PBS with 0.1% Tween and 10% goat serum. Sections were incubated for 1 hr at room temperature with biotinylated secondary antibody diluted in 0.1% PBS-Tween. DAB staining was performed according to the Vectastain ABC kit instructions (Vector Laboratories). For each animal, three tissue sections from one level of striatum was stained and analyzed for TH-positive fiber innervation. To achieve a TH cell count representative of the whole SN, each animal was analysed at four and three rostrocaudal levels (bregma −4.80 to −6.04). Two tissue sections from each level were quantified by immunohistochemistry.

Data were analysed using a one-way ANOVA with post-hoc Bonferroni tests. The results are illustrated in FIGS. 1 to 7.

CONCLUSION

The results demonstrate that both GLP-1/GIP dual agonist peptides (DA1 (SEQ ID NO. 1) and DA2 (SEQ ID NO. 2)) showed superior properties over single GLP-1 and GIP analogues in animal models of Alzheimer's and Parkinson's disease. Thus, the data of the present examples demonstrate that both peptides DA1 (SEQ ID NO. 1) and DA2 (SEQ ID NO. 2) may be considered suitable for use in the treatment and/or lessening the likelihood of occurrence, or even prevention of neurodegenerative disorders such as, for example, Alzheimer's Disease and/or Parkinson's Disease.

REFERENCES

Aviles-Olmos I, Dickson J, Kefalopoulou Z, Djamshidian A, Ell P, Soderlund T, Whitton P, Wyse R, Isaacs T, Lees A, Limousin P, Foltynie T (2013) Exenatide and the treatment of patients with Parkinson's disease. The Journal of clinical investigation. 123:2730-6.

Aviles-Olmos I, Dickson J, Kefalopoulou Z, Djamshidian A, Kahan J, Fmedsci P E, Whitton P, Wyse R, Isaacs T, Lees A, Limousin P, Foltynie T (2014) Motor and Cognitive Advantages Persist 12 Months After Exenatide Exposure in Parkinson's Disease. Journal of Parkinson's disease. DOI: 10.3233/JPD-140364.

Baggio L L, Drucker D J (2007) Biology of incretins: GLP-1 and GIP. Gastroenterology 132:2131-2157.

Bertilsson G, Patrone C, Zachrisson O, Andersson A, Dannaeus K, Heidrich J, Kortesmaa J, Mercer A, Nielsen E, Ronnholm H, Wikstrom L (2008) Peptide hormone exendin-4 stimulates subventricular zone neurogenesis in the adult rodent brain and induces recovery in an animal model of Parkinson's disease. Journal of neuroscience research 86:326-338.

Blennow K, de Leon M J, Zetterberg H (2006) Alzheimer's disease. Lancet 368:387-403.

Bliss T V P, Collingridge G L (1993) A synaptic model of memory: long-term potentiation in the hippocampus. Nature 361:31-39.

Bomfim T R, Forny-Germano L, Sathler L B, Brito-Moreira J, Houzel J C, Decker H, Silverman M A, Kazi H, Melo H M, McClean P L, Hölscher C, Arnold S E, Talbot K, Klein W L, Munoz D P, Ferreira S T, De Felice F G (2012) An anti-diabetes agent protects the mouse brain from defective insulin signaling caused by Alzheimer's disease-associated Abeta oligomers. The Journal of clinical investigation. 122:1339-53

Campbell J E, Drucker D J (2013) Pharmacology, physiology, and mechanisms of incretin hormone action. Cell metabolism 17:819-837.

Cereda E, Barichella M, Cassani E, Caccialanza R, Pezzoli G (2012) Clinical features of Parkinson disease when onset of diabetes came first: A case-control study. Neurology 78:1507-1511.

Cleary J P, Walsh D M, Hofmeister J J, Shankar G M, Kuskowski M A, Selkoe D J, Ashe K H (2005) Natural oligomers of the amyloid-beta protein specifically disrupt cognitive function. Nature neuroscience 8:79-84.

Duffy A M, Hölscher C (2013a) Novel GIP incretin analogues as a potential treatment for Alzheimer disease. In: Society for Neuroscience conference, p abstr. 41.23 San Diego.

Duffy A M, Hölscher C (2013b) The incretin analogue D-Ala(2)GIP reduces plaque load, astrogliosis and oxidative stress in an APP/PS1 mouse model of Alzheimer's disease. Neuroscience 228:294-300.

Elkinson S, Keating G M (2013) Lixisenatide: first global approval. Drugs 73:383-391.

Faivre E, Hölscher C (2013a) D-Ala2GIP facilitated synaptic plasticity and reduces plaque load in aged wild type mice and in an Alzheimer's disease mouse model. Journal of Alzheimer's disease: JAD 35:267-283.

Faivre E, Hölscher C (2013b) Neuroprotective effects of D-Ala2GIP on Alzheimer's disease biomarkers in an APP/PS1 mouse model. Alzheimer's research & therapy 5:20-48.

Faivre E, Gault V A, Thorens B, Hölscher C (2011) Glucose-dependent insulinotropic polypeptide receptor knockout mice are impaired in learning, synaptic plasticity, and neurogenesis. J Neurophysiol 105:1574-1580.

Finan B et al. (2013) Unimolecular dual incretins maximize metabolic benefits in rodents, monkeys, and humans. Science translational medicine 5:209ra151.

Gault V, Hölscher C (2008a) GLP-1 agonists facilitate hippocampal LTP and reverse the impairment of LTP induced by beta-amyloid. European journal of pharmacology 587:112-117.

Gault V A, Hölscher C (2008b) Protease-resistant glucose-dependent insulinotropic polypeptide agonists facilitate hippocampal LTP and reverse the impairment of LTP induced by beta-amyloid. J Neurophysiol 99:1590-1595.

Gault V A, Flatt P R, O'Harte F P (2003) Glucose-dependent insulinotropic polypeptide analogues and their therapeutic potential for the treatment of obesity-diabetes. Biochemical and biophysical research communications 308:207-213.

Gengler S, McClean P, McCurtin R, Gault V, Hölscher C (2012) Val(8)GLP-1 rescues synaptic plasticity and reduces dense core plaques in APP/PS1 mice. Neurobiology of aging 33:265-276.

Han B, Hu J, Shen J, Gao Y, Lu Y, Wang T (2013) Neuroprotective effect of hydroxysafflor yellow A on 6-hydroxydopamine-induced Parkinson's disease in rats. European journal of pharmacology 714:83-88.

Harkavyi A, Abuirmeileh A, Lever R, Kingsbury A E, Biggs C S, Whitton P S (2008) Glucagon-like peptide 1 receptor stimulation reverses key deficits in distinct rodent models of Parkinson's disease. Journal of neuroinflammation 5:19.

Hölscher C (2014) Insulin, incretins and other growth factors as potential novel treatments for Alzheimer's and Parkinson's diseases. Biochemical Society transactions 42:593-599.

Irwin N, O'Harte F P, Gault V A, Green B D, Greer B, Harriott P, Bailey C J, Flatt P R (2006) GIP(Lys(16)PAL) and GIP(Lys(37)PAL): Novel Long-Acting Acylated Analogues of Glucose-Dependent Insulinotropic Polypeptide with Improved Antidiabetic Potential. Journal of medicinal chemistry 49:1047-1054.

LaFerla F M, Oddo S (2005) Alzheimer's disease: Abeta, tau and synaptic dysfunction. Trends Mol Med 11:170-176.

Li Y, Perry T, Kindy M S, Harvey B K, Tweedie D, Holloway H W, Powers K, Shen H, Egan J M, Sambamurti K, Brossi A, Lahiri D K, Mattson M P, Hoffer B J, Wang Y, Greig N H (2009) GLP-1 receptor stimulation preserves primary cortical and dopaminergic neurons in cellular and rodent models of stroke and Parkinsonism. Proceedings of the National Academy of Sciences of the United States of America. 106:1285-90.

Lovshin J A, Drucker D J (2009) Incretin-based therapies for type 2 diabetes mellitus. Nature reviews Endocrinology 5:262-269.

Luchsinger J A, Tang M X, Shea S, Mayeux R (2004) Hyperinsulinemia and risk of Alzheimer disease. Neurology 63:1187-1192.

Madsen et al; Journal of Medicinal Chemistry, 2007, 50, (24), 6126-6132.

Martin C M, Irwin N, Flatt P R, Gault V A (2013) A novel acylated form of (d-Ala(2))GIP with improved antidiabetic potential, lacking effect on body fat stores. Biochimica et biophysica acta 1830:3407-3413.

McClean P, Hölscher C (2013) Liraglutide can reverse memory impairment, synaptic loss and reduce plaque load in aged APP/PS1 mice, a model of Alzheimer's disease. Neuropharmacol DOI::10.1016/j.neuropharm.2013.1008.1005.

McClean P, Parthsarathy V, Faivre E, Hölscher C (2011) The diabetes drug Liraglutide prevents degenerative processes in a mouse model of Alzheimer's disease. The Journal of neuroscience. 31:6587-6594.

McClean P L, Gault V A, Harriott P, Hölscher C (2010) Glucagon-like peptide-1 analogues enhance synaptic plasticity in the brain: A link between diabetes and Alzheimer's disease. European journal of pharmacology 630:158-162.

Moloney A M, Griffin R J, Timmons S, O'Connor R, Ravid R, O'Neill C (2010) Defects in IGF-1 receptor, insulin receptor and IRS-1/2 in Alzheimer's disease indicate possible resistance to IGF-1 and insulin signalling. Neurobiology of aging 31:224-243.

Morris J K, Bomhoff G L, Gorres B K, Davis V A, Kim J, Lee P P, Brooks W M, Gerhardt G A, Geiger P C, Stanford J A (2011) Insulin resistance impairs nigrostriatal dopamine function. Experimental neurology 231:171-180.

Nyberg J, Jacobsson C, Anderson M F, Eriksson P S (2007) Immunohistochemical distribution of glucose-dependent insulinotropic polypeptide in the adult rat brain. Journal of neuroscience research 85:2099-2119.

Ohara T, Doi Y, Ninomiya T, Hirakawa Y, Hata J, Iwaki T, Kanba S, Kiyohara Y (2011) Glucose tolerance status and risk of dementia in the community: The Hisayama Study. Neurology 77:1126-1134.

Radde R, Bolmont T, Kaeser S A, Coomaraswamy J, Lindau D, Stoltze L, Calhoun M E, Jaggi F, Wolburg H, Gengler S, Haass C, Ghetti B, Czech C, Hölscher C, Mathews P M, Jucker M (2006) Abeta42-driven cerebral amyloidosis in transgenic mice reveals early and robust pathology. EMBO Rep 7:940-647.

Ristow M (2004) Neurodegenerative disorders associated with diabetes mellitus. J Mol Med 82:510-529.

Shen J (2010) Impaired neurotransmitter release in Alzheimer's and Parkinson's diseases. Neuro-degenerative diseases 7:80-83.

Talbot K, Wang H Y, Kazi H, Han L Y, Bakshi K P, Stucky A, Fuino R L, Kawaguchi K R, Samoyedny A J, Wilson R S, Arvanitakis Z, Schneider J A, Wolf B A, Bennett D A, Trojanowski J Q, Arnold S E (2012) Demonstrated brain insulin resistance in Alzheimer's disease patients is associated with IGF-1 resistance, IRS-1 dysregulation, and cognitive decline. The Journal of clinical investigation. 122:1316-38.

What is claimed is:

1. A method of treating and/or lessening the likelihood of occurrence of a neurological disorder selected from the group consisting of clinical or pre-clinical Alzheimer's disease, prodromal Alzheimer's disease, clinical or preclinical amyloid angiopathy (CAA) and/or Parkinson's disease comprising administering to a patient in need thereof a pharmaceutical composition comprising a GIP/GLP-1 co-agonist peptide or a pharmaceutically acceptable salt or solvate of the peptide, wherein said co-agonist peptide comprises the amino acid sequence of general Formula I:

(SEQ ID No. 12)
Tyr-Aib-Glu-Gly-Thr-Phe-Thr-Ser-Asp-Tyr-Ser-Ile-

Tyr-Leu-Asp-Lys-Gln-Ala-Ala-Aib-Glu-Phe-Val-

Xaa$^{24}$-Trp-Leu-Leu-Ala-Gly-Y1-R$^2$ wherein

Xaa$^{24}$ is selected from Asn and Cys; wherein if Xaa$^{24}$ is Cys, Xaa$^{24}$ may comprise a hydrophilic moiety covalently linked thereto;

Y1 is selected from absent or an extension comprising at least nine amino acid molecules; and R$^2$ is selected from —NH$_2$ and —OH.

2. The method according to claim 1, wherein Y1 is Gly-Pro-Ser-Ser-Gly-Ala-Pro-Pro-Pro-Ser (SEQ ID No. 3).

3. The method according to claim 1, wherein Y1 is Gly-Pro-Ser-Ser-Gly-Ala-Pro-Pro-Pro-Ser-Cys (SEQ ID No. 5).

4. The method according to claim 1, wherein Y1 is Gly-Pro-Ser-Ser-Gly-Ala-Pro-Pro-Pro-Ser-Lys (SEQ ID No. 4).

5. The method according to claim 1, wherein said co-agonist peptide comprises the following sequence:

(SEQ ID NO. 1)
YXEGTFTSDYSIYLDKQAAXEFVNWLLAGGPSSGAPPP

S[Lys-C16]-NH$_2$, wherein C16 is a saturated fatty acid and wherein X is amino-isobutyric acid.

6. The method according to claim 5, wherein C16 is palmitate.

7. The method according to claim 1, wherein said co-agonist peptide comprises the following sequence:

```
                                             (SEQ ID NO 2)
YXEGTFTSDYSIYLDKQAAXEFV[Cys-40 kDaPEG]WLLAGGPSSGA

PPPS[Lys-γE-C16]-NH2
``` wherein C16 is a saturated fatty acid and X is aminoisobutyric acid.

8. The method according to claim 7, wherein C16 is palmitate.

9. The method according to claim 7, wherein 40 kDaPEG is a polyethylene glycol molecule having an average molecular weight of 40 kDa.

10. The method according to claim 1, wherein the neurological disorder is a dysfunctional cognitive process.

11. The method according to claim 10, wherein the dysfunctional cognitive process is selected from the group consisting of attention, calculation, memory, judgment, insight, learning and reasoning.

12. The method according to claim 1, wherein the neurological disorder is Parkinson's Disease Dementia (PDD).

13. The method according to claim 1, wherein the neurological disorder is caused by or associated with long-term potentiation (LTP) of synaptic transmission.

* * * * *